(12) United States Patent
Koch et al.

(10) Patent No.: US 9,340,604 B1
(45) Date of Patent: May 17, 2016

(54) HUMAN MONOCLONAL ANTIBODY SPECIFIC FOR THE F PROTEIN OF RESPIRATORY SYNCYTIAL VIRUS (RSV)

(71) Applicant: Aridis Pharmaceuticals, Inc., San Jose, CA (US)

(72) Inventors: Holger Koch, Zurich (CH); Simon Urwyler, Bern (CH); Michael P. Rudolf, Ittigen (CH); Vu L. Truong, Campbell, CA (US)

(73) Assignee: Aridis Pharmaceuticals, Inc., San Jose, CA (US)

( * ) Notice: Subject to any disclaimer, the term of this patent is extended or adjusted under 35 U.S.C. 154(b) by 0 days.

(21) Appl. No.: 14/527,545

(22) Filed: Oct. 29, 2014

(51) Int. Cl.
*A61K 39/42* (2006.01)
*C07K 16/00* (2006.01)
*C07K 16/10* (2006.01)

(52) U.S. Cl.
CPC ......... *C07K 16/1027* (2013.01); *C07K 2317/21* (2013.01); *C07K 2317/76* (2013.01)

(58) Field of Classification Search
None
See application file for complete search history.

(56) References Cited

U.S. PATENT DOCUMENTS 8,119,406 B2  2/2012  Shaaltiel et al.
8,513,397 B2  8/2013  Mason et al.

OTHER PUBLICATIONS

Rudikoff et al Proc Natl Acad Sci USA 1982 vol. 79 p. 1979.*
Kwakkenbos, et al., Nature Medicine 16, 123-128 (2010).*
Adams, et al. (2010) "Palivizumab-resistant human respiratory syncytial virus infection in infancy." *Clin Infect Dis.*, 51(2): 185-8.
Beerli, et al. (2008) "Isolation of Human Monoclonal Antibodies by Mammalian Cell Display," *Proc Natl Acad Sci U S A.*, 105(38): 14336-41.
Boeckh, et al. (2001) "Phase 1 evaluation of the respiratory syncytial virus-specific monoclonal antibody palivizumab in recipients of hematopoietic stem cell transplants." *J Infect Dis.*, 184(3): 350-354.
Fuss, et al. (2009) "Isolation of Whole Mononuclear Cells from Peripheral Blood and Cord Blood." *Current Protocols in Immunology.* Section 1, Unit 7.1, pp. 7.1.1-7.1.8.
Hierholzer, et al. (1996) "Preparation of antigens." *Virology Methods Manual*, Mahy and Kangro, eds., Academic Press, London, pp. 47-70.
Lang, et al. (2004) "Prophylaxis and therapy of Pseudomonas aeruginosa infection in cystic fibroses and immunocompromised patients." *Vaccine*, 11: S44-S48.
Liu, et al. (2010) "Recovery and purification process development for monoclonal antibody production." *mAbs*, 2(5): 480-499.
McLellan, et al. (2010) "Structure of a Major Antigenic Site on the Respiratory Syncytial Virus Fusion Glycoprotein in Complex with Neutralizing Antibody 101F." *J Virol.*, 84(23): 12236-12244.
McLellan, et al. (2010) "Structural basis of respiratory syncytial virus neutralization by motavizumab." *Nat Struct Mol Biol.*, 17(2): 248-250.
Welschof, et al. (1995) "Amino acid sequence based PCR primers for amplification of rearranged human heavy and light chain immunoglobulin variable regions." *J Immunol Methods*, 179(2): 203-214.
Zhao, et al. (2004) "Variable resistance to palivizumab in cotton rats by respiratory syncytial virus mutants." *J Infect Dis.*, 190(11): 1941-1946.
Zhu, et al. (2011) "Analysis of respiratory syncytial virus preclinical and clinical variants resistant to neutralization by monoclonal antibodies palivizumab and/or motavizumab." *J Infect Dis.*, 203(5): 674-682.

\* cited by examiner

*Primary Examiner* — Shanon A Foley
*Assistant Examiner* — Myron Hill
(74) *Attorney, Agent, or Firm* — Quine Intellectual Property Law Group, P.C.

(57) ABSTRACT

This invention is directed to an antibody construct or fragment thereof derived from an RSV-infected human, such that the antibody construct binds with specificity to RSV fusion protein antigenic region II/A with an affinity of greater than $1 \times 10^{-9}$ M. Preferably, the antibody construct is capable of neutralizing RSV strains, including at least one RSV strain that is resistant to palivizumab. The invention further relates to nucleic acids encoding the antibody construct or portions thereof, and cell lines expressing the antibody. This invention further relates to methods for producing said antibody construct, and to the use of said antibody construct for treating or preventing infection of a patient by RSV having a normal or mutated version of F protein.

26 Claims, 9 Drawing Sheets

FIGURE 1

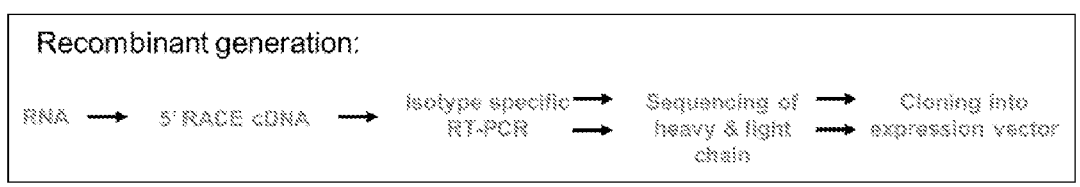

FIGURE 2

AR201 heavy chain variable region

```
  1    L   V   Q   L   R   E   S   G   P   G   L   V   K   P   S   Q   T   L   S   L
  1   CTGGTGCAGCTGCGGGAGTCGGGCCCAGGACTGGTGAAGCCTTCACAGACCCTGTCCCTC

21    T   C   S   V   S   G   A   S   I   N   L   Y   D   Y   F   W   G   W   I   R
 61   ACCTGCAGTGTCTCTGGAGCCTCCATCAACCTCTATGATTACTTCTGGGGTTGGATCCGT

41    Q   A   P   G   R   G   P   E   W   I   G   Y   I   S   G   S   T   Y   Y   N
121   CAGGCCCCAGGGAGGGGCCCAGAATGGATTGGGTACATCAGTGGGAGCACCTACTACAAC

61    P   S   L   K   R   R   A   T   I   S   V   D   T   S   K   S   Q   F   F   L
181   CCGTCCCTCAAGAGACGCGCTACCATCTCGGTTGACACGTCCAAGAGCCAGTTCTTCCTG

81    E   L   T   S   V   T   A   A   D   T   A   V   Y   Y   C   A   R   D   V   G
241   GAGCTGACCTCTGTCACTGCCGCAGACACGGCCGTGTATTACTGTGCCAGAGATGTGGGG

101    W   G   P   Q   Y   Y   Y   G   L   D   V   W   G   Q   G   T   T   V   T   V
301   TGGGGCCCCCAGTACTACTACGGTCTGGACGTCTGGGGCCAAGGGACCACGGTCACCGTC

121    S   S       (SEQ ID NO.:1)
361   TCCTCA        (SEQ ID NO.:2)
```

FIGURE 3

AR201 light chain (kappa) variable region

```
  1   D   L   V   L   T   Q   S   P   G   T   L   S   L   S   P   G   E   R   A   T
  1   GACCTTGTGTTGACGCAGTCTCCAGGCACCCTGTCTTTGTCTCCAGGGGAAAGGGCCACC

21   L   S   C   R   A   S   H   S   V   Q   S   T   S   L   A   W   Y   Q   Q   K
 61   CTCTCCTGCAGGGCCAGTCACAGTGTTCAAAGCACCTCCCTAGCCTGGTACCAGCAGAAA

41   R   G   Q   A   P   R   L   L   I   Y   G   G   S   S   R   V   T   G   I   P
121   CGTGGCCAGGCTCCCAGACTCCTCATCTATGGTGGATCCAGCAGGGTCACTGGCATCCCA

61   D   R   F   S   G   S   G   S   G   T   D   F   T   L   T   I   S   R   L   E
181   GACAGGTTCAGTGGCAGTGGGTCTGGGACAGACTTCACTCTCACCATCAGCAGACTGGAG

81   P   E   D   F   A   V   Y   Y   C   Q   Q   S   D   R   S   P   P   I   T   F
241   CCTGAAGATTTTGCAGTGTATTACTGTCAGCAGTCTGATAGGTCGCCCCCGATCACCTTC

101   G   Q   G   T   R   L   E   M   K        (SEQ ID NO.:3)
301   GGCCAAGGGACACGACTGGAGATGAAAC             (SEQ ID NO.:4)
```

FIGURE 4

CDR nucleotide sequences of AR201 heavy chain

CDR1: (SEQ ID NO.: 5)    76 GGAGCCTCCATCAACCTCTATGAT 99

CDR2: (SEQ ID NO.: 6)    151 GGGTACATCAGTGGGAGCACC 171

CDR3: (SEQ ID NO.: 7)    285 GCCAGAGATGTGGGGTGGGGCCCCCA GTACTACTACGGTCTGGACGTC 332

CDR amino acid sequences of AR201 heavy chain

CDR1: (SEQ ID NO.: 8)    26 GASINLYD 33

CDR2: (SEQ ID NO.: 9)    51 GYISGST 57

CDR3: (SEQ ID NO.: 10)   96 ARDVGWGPQYYYGLDV 111

CDR nucleotide sequences of AR201 kappa light chain

CDR1: (SEQ ID NO.: 11)   78 CACAGTGTTCAAAGCACCTCC 98

CDR2: (SEQ ID NO.: 12)   151 GGTGGATCC 159

CDR3: (SEQ ID NO.: 13)   268 CAGCAGTCTGATAGGTCGCCCCCGATCACC 297

CDR amino acid sequences of AR201 kappa light chain

CDR1: (SEQ ID NO.: 14)   27 HSVQSTS 33

CDR2: (SEQ ID NO.: 15)   51 GGS 53

CDR3: (SEQ ID NO.: 16)   90 QQSDRSPPIT 99

FIGURE 9A

F protein of clinical isolate #20 (SEQ ID NO.: 17)

```
ATGGAGTTGC CAATCCTCAA AACAAATGCA ATTACCACAA TCCTTGCTGC AGTCTTACTC 60
TGTTTCGCTT CCAGTCAAAA CATCACTGAA GAATTTTATC AATCAACATG CAGTGCAGTT 120
AGCAAAGGCT ATCTTAGTGC TTTAAGAACT GGTTGGTATA CTAGTGTTAT AACTATAGAA 180
TTAAGTAATA TCAAGGAAAA TAAGTGTAAT GGAACAGACG CTAAGGCAAA ATTGATAAAA 240
CAAGAATTAG ATAAATATAA AAATGCTGTA ACAGAATTGC AGTTGCTCAT GCAAAGCACA 300
CCAGCAGCCA ACAATCGAGC CAGAAGAGAA CTACCAAGGT TTATGAATTA TACACTCAAC 360
AATACCAAAA ATAACAATGT AACATTAAGC AAGAAAAGGA AAAGAAGATT TCTTGGCTTT 420
TTGTTAGGTG TTGGATCTGC AATCGCCAGT GGCATTGCTG TATCTAAAGT CCTGCACCTA 480
GAAGGGGAAG TGAACAAAAT AAAAAGTGCT CTACTATCCA CAAACAAGGC TGTAGTCAGC 540
TTATCAAATG GAGTTAGTGT CTTAACCAGC AAAGTGTTAG ACCTCAAAAA CTATATAGAT 600
AAACAGTTGT TACCCATTGT GAACAAGCAA AGCTGCAGCA TATCAAACAT TGAAACTGTG 660
ATAGAATTCC AACAAAAGAA CAACAGACTA CTAGAGATTA CCAGGGAATT CAGTGTTAAT 720
GCAGGTGTAA CTACACCTGT AAGCACTTAC ATGTTAACAA ATAGTGAATT ATTATCATTA 780
ATCAATGATA TGCCTATAAC AAATGATCAG AAAAATTTAA TGTCTAACAA TGTTCAAATA 840
GTTAGACAGC AAAGTTACTC TATCATGTCC ATAATAAAGG AGGAAGTCTT AGCATATGTA 900
GTACAATTAC CACTATATGG TGTAATAGAT ACACCTTGTT GGAAATTACA CACATCCCCT 960
CTATGCACAA CCAACACAAA GGAAGGGTCC AACATCTGTT TAACAAGAAC CGACAGAGGA 1020
TGGTACTGTG ACAATGCAGG ATCAGTTTCT TTCTTCCCAC AAGCTGAAAC ATGCAAAGTT 1080
CAATCGAATC GAGTATTTTG TGACACAATG AACAGTTTAA CATTACCAAG TGAAGTAAAC 1140
CTCTGCAACA TTGACATATT CAACCCTAAA TATGATTGCA AAATTATGAC TTCAAAAACA 1200
GATGTAAGCA GCTCCGTTAT CACATCTCTA GGAGCCATTG TGTCATGCTA TGGCAAAACT 1260
AAATGTACAG CATCCAATAA AAATCGTGGA ATCATAAAGA CATTTTCTAA CGGGTGTGAT 1320
TATGTATCAA ATAAGGGGGT GGACACTGTA TCTGTAGGTA ATACATTATA TTATGTAAAT 1380
AAGCAAGAAG GAAAAAGTCT CTATGTAAAA GGTGAACCAA TAATAAATTT CTATGACCCA 1440
TTAGTGTTCC CTTCTGATGA ATTTGATGCA TCAATATCTC AAGTCAATGA GAAGATTAAC 1500
CAGAGCCTAG CATTTATTCG TAAATCCGAT GAATTATTAC ATAATGTAAA TGTTGGTAAA 1560
TCCACCACAA ATATCATGAT AACTACTATA ATTATAGTGA TTATAGTAAT ATTGTTATTA 1620
TTAATTGCAG TTGGGCTGTT CCTATACTGC AAGGCCAGAA GCACACCAGT CACACTAAGC 1680
AAGGATCAAC TGAGTGGTAT AAATAATATT GCATTAGTA AC
```

FIGURE 9B

Amino acid sequence clinical isolate #20 | 574 aa (SEQ ID NO.: 18)

```
MELPILKTNAITTILAAVLLCFASSQNITEEFYQSTCSAVSKGYLSALRTGWYTSVITIE  60
LSNIKENKCNGTDAKAKLIKQELDKYKNAVTELQLLMQSTPAANNRARRELPRFMNYTLN  120
NTKNNNVTLSKKRKRRFLGFLLGVGSAIASGIAVSKVLHLEGEVNKIKSALLSTNKAVVS  180
LSNGVSVLTSKVLDLKNYIDKQLLPIVNKQSCSISNIETVIEFQQKNNRLLEITREFSVN  240
AGVTTPVSTYMLTNSELLSLINDMPITNDQKNLMSNNVQIVRQQSYSIMSIIKEEVLAYV  300
VQLPLYGVIDTPCWKLHTSPLCTTNTKEGSNICLTRTDRGWYCDNAGSVSFFPQAETCKV  360
QSNRVFCDTMNSLTLPSEVNLCNIDIFNPKYDCKIMTSKTDVSSSVITSLGAIVSCYGKT  420
KCTASNKNRGIIKTFSNGCDYVSNKGVDTVSVGNTLYYVNKQEGKSLYVKGEPIINFYDP  480
LVFPSDEFDASISQVNEKINQSLAFIRKSDELLHNVNVGKSTTNIMITTIIIVIIVILLL  540
LIAVGLFLYCKARSTPVTLSKDQLSGINNIAFSN  574
```

FIGURE 10

Epitope for palivizumab (SEQ ID NO: 23)

240 AGVTTPVSTY MLTNSELLSL INDMPITNDQ K*K*LMSNNVQI 280

Corresponding sequence of palivizumab resistant clinical isolate #20 (SEQ ID NO: 24)

240 AGVTTPVSTY MLTNSELLSL INDMPITNDQ K*N*LMSNNVQI 280

FIGURE 11

Predicted peptides for Asp-N digestion containing fragments of palivizumab epitope amino acids 254-277 of RSV F protein [underlined]

Peptide 200-262: (SEQ ID NO.: 25)

DKQLLPIVNKQSCSISNIETVIEFQQKNNRLLEITREFSVNAGVTTPVSTYMLTNSELLSLI
[MW 7093.72]

Peptide 269-309: (SEQ ID NO.: 26)

DQKKLMSNNVQIVRQQSYSIMSIIKEEVLAYVVQLPLYGVI
[MW4737.57]

FIGURE 12

```
                          SEQUENCE LISTING

<160> NUMBER OF SEQ ID NOS: 26

<210> SEQ ID NO 1
<211> LENGTH: 122
<212> TYPE: PRT
<213> ORGANISM: Homo sapiens

<400> SEQUENCE: 1

Leu Val Gln Leu Arg Glu Ser Gly Pro Gly Leu Val Lys Pro Ser Gln
1               5                   10                  15

Thr Leu Ser Leu Thr Cys Ser Val Ser Gly Ala Ser Ile Asn Leu Tyr
            20                  25                  30

Asp Tyr Phe Trp Gly Trp Ile Arg Gln Ala Pro Gly Arg Gly Pro Glu
        35                  40                  45

Trp Ile Gly Tyr Ile Ser Gly Ser Thr Tyr Tyr Asn Pro Ser Leu Lys
    50                  55                  60

Arg Arg Ala Thr Ile Ser Val Asp Thr Ser Lys Ser Gln Phe Phe Leu
65                  70                  75                  80

Glu Leu Thr Ser Val Thr Ala Ala Asp Thr Ala Val Tyr Tyr Cys Ala
                85                  90                  95

Arg Asp Val Gly Trp Gly Pro Gln Tyr Tyr Gly Leu Asp Val Trp
            100                 105                 110

Gly Gln Gly Thr Thr Val Thr Val Ser Ser
            115                 120

<210> SEQ ID NO 2
<211> LENGTH: 366
<212> TYPE: DNA
<213> ORGANISM: Homo sapiens
<220> FEATURE:
<221> NAME/KEY: CDS
<222> LOCATION: (1)..(366)

<400> SEQUENCE: 2 ctg gtg cag ctg cgg gag tcg ggc cca gga ctg gtg aag cct tca cag        48
Leu Val Gln Leu Arg Glu Ser Gly Pro Gly Leu Val Lys Pro Ser Gln
1               5                   10                  15 acc ctg tcc ctc acc tgc agt gtc tct gga gcc tcc atc aac ctc tat        96
Thr Leu Ser Leu Thr Cys Ser Val Ser Gly Ala Ser Ile Asn Leu Tyr
            20                  25                  30 gat tac ttc tgg ggt tgg atc cgt cag gcc cca ggg agg ggc cca gaa       144
Asp Tyr Phe Trp Gly Trp Ile Arg Gln Ala Pro Gly Arg Gly Pro Glu
        35                  40                  45 tgg att ggg tac atc agt ggg agc acc tac tac aac ccg tcc ctc aag       192
Trp Ile Gly Tyr Ile Ser Gly Ser Thr Tyr Tyr Asn Pro Ser Leu Lys
    50                  55                  60 aga cgc gct acc atc tcg gtt gac acg tcc aag agc cag ttc ttc ctg       240
Arg Arg Ala Thr Ile Ser Val Asp Thr Ser Lys Ser Gln Phe Phe Leu
65                  70                  75                  80 gag ctg acc tct gtc act gcc gca gac acg gcc gtg tat tac tgt gcc       288
Glu Leu Thr Ser Val Thr Ala Ala Asp Thr Ala Val Tyr Tyr Cys Ala
                85                  90                  95 aga gat gtg ggg tgg ggc ccc cag tac tac ggt ctg gac gtc tgg            336
Arg Asp Val Gly Trp Gly Pro Gln Tyr Tyr Gly Leu Asp Val Trp
            100                 105                 110 ggc caa ggg acc acg gtc acc gtc tcc tca                                366
Gly Gln Gly Thr Thr Val Thr Val Ser Ser
            115                 120
```

<210> SEQ ID NO 3
<211> LENGTH: 109
<212> TYPE: PRT
<213> ORGANISM: Homo sapiens

<400> SEQUENCE: 3

Asp Leu Val Leu Thr Gln Ser Pro Gly Thr Leu Ser Leu Ser Pro Gly
1               5                   10                  15

Glu Arg Ala Thr Leu Ser Cys Arg Ala Ser His Ser Val Gln Ser Thr
            20                  25                  30

Ser Leu Ala Trp Tyr Gln Gln Lys Arg Gly Gln Ala Pro Arg Leu Leu
        35                  40                  45

Ile Tyr Gly Gly Ser Ser Arg Val Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Ser Asp Arg Ser Pro
                85                  90                  95

Pro Ile Thr Phe Gly Gln Gly Thr Arg Leu Glu Met Lys
            100                 105

<210> SEQ ID NO 4
<211> LENGTH: 328
<212> TYPE: DNA
<213> ORGANISM: Homo sapiens
<220> FEATURE:
<221> NAME/KEY: CDS
<222> LOCATION: (1)..(327)

<400> SEQUENCE: 4 gac ctt gtg ttg acg cag tct cca ggc acc ctg tct ttg tct cca ggg    48
Asp Leu Val Leu Thr Gln Ser Pro Gly Thr Leu Ser Leu Ser Pro Gly
1               5                   10                  15 gaa agg gcc acc ctc tcc tgc agg gcc agt cac agt gtt caa agc acc    96
Glu Arg Ala Thr Leu Ser Cys Arg Ala Ser His Ser Val Gln Ser Thr
            20                  25                  30 tcc cta gcc tgg tac cag cag aaa cgt ggc cag gct ccc aga ctc ctc   144
Ser Leu Ala Trp Tyr Gln Gln Lys Arg Gly Gln Ala Pro Arg Leu Leu
        35                  40                  45 atc tat ggt gga tcc agc agg gtc act ggc atc cca gac agg ttc agt   192
Ile Tyr Gly Gly Ser Ser Arg Val Thr Gly Ile Pro Asp Arg Phe Ser
    50                  55                  60 ggc agt ggg tct ggg aca gac ttc act ctc acc atc agc aga ctg gag   240
Gly Ser Gly Ser Gly Thr Asp Phe Thr Leu Thr Ile Ser Arg Leu Glu
65                  70                  75                  80 cct gaa gat ttt gca gtg tat tac tgt cag cag tct gat agg tcg ccc   288
Pro Glu Asp Phe Ala Val Tyr Tyr Cys Gln Gln Ser Asp Arg Ser Pro
                85                  90                  95 ccg atc acc ttc ggc caa ggg aca cga ctg gag atg aaa c             328
Pro Ile Thr Phe Gly Gln Gly Thr Arg Leu Glu Met Lys
            100                 105

<210> SEQ ID NO 5
<211> LENGTH: 24
<212> TYPE: DNA
<213> ORGANISM: Homo sapiens

<400> SEQUENCE: 5
ggagcctcca tcaacctcta tgat                                         24

```
<210> SEQ ID NO 6
<211> LENGTH: 21
<212> TYPE: DNA
<213> ORGANISM: Homo sapiens

<400> SEQUENCE: 6
gggtacatca gtgggagcac c                                              21

<210> SEQ ID NO 7
<211> LENGTH: 48
<212> TYPE: DNA
<213> ORGANISM: Homo sapiens

<400> SEQUENCE: 7
gccagagatg tggggtgggg cccccagtac tactacggtc tggacgtc                 48

<210> SEQ ID NO 8
<211> LENGTH: 8
<212> TYPE: PRT
<213> ORGANISM: Homo sapiens

<400> SEQUENCE: 8

Gly Ala Ser Ile Asn Leu Tyr Asp
1               5

<210> SEQ ID NO 9
<211> LENGTH: 7
<212> TYPE: PRT
<213> ORGANISM: Homo sapiens

<400> SEQUENCE: 9

Gly Tyr Ile Ser Gly Ser Thr
1               5

<210> SEQ ID NO 10
<211> LENGTH: 16
<212> TYPE: PRT
<213> ORGANISM: Homo sapiens

<400> SEQUENCE: 10

Ala Arg Asp Val Gly Trp Gly Pro Gln Tyr Tyr Tyr Gly Leu Asp Val
1               5                   10                  15

<210> SEQ ID NO 11
<211> LENGTH: 21
<212> TYPE: DNA
<213> ORGANISM: Homo sapiens

<400> SEQUENCE: 11
cacagtgttc aaagcacctc c                                              21

<210> SEQ ID NO 12
<211> LENGTH: 9
<212> TYPE: DNA
<213> ORGANISM: Homo sapiens

<400> SEQUENCE: 12 ggtggatcc                                                             9

<210> SEQ ID NO 13
<211> LENGTH: 30
<212> TYPE: DNA
<213> ORGANISM: Homo sapiens
```

<400> SEQUENCE: 13
cagcagtctg ataggtcgcc cccgatcacc                                            30

<210> SEQ ID NO 14
<211> LENGTH: 7
<212> TYPE: PRT
<213> ORGANISM: Homo sapiens

<400> SEQUENCE: 14

His Ser Val Gln Ser Thr Ser
1               5

<210> SEQ ID NO 15
<211> LENGTH: 3
<212> TYPE: PRT
<213> ORGANISM: Homo sapiens

<400> SEQUENCE: 15

Gly Gly Ser
1

<210> SEQ ID NO 16
<211> LENGTH: 10
<212> TYPE: PRT
<213> ORGANISM: Homo sapiens

<400> SEQUENCE: 16

Gln Gln Ser Asp Arg Ser Pro Pro Ile Thr
1               5                   10

<210> SEQ ID NO 17
<211> LENGTH: 1722
<212> TYPE: DNA
<213> ORGANISM: Respiratory syncytial virus

<400> SEQUENCE: 17
atggagttgc caatcctcaa aacaaatgca attaccacaa tccttgctgc agtcttactc      60
tgtttcgctt ccagtcaaaa catcactgaa gaattttatc aatcaacatg cagtgcagtt     120
agcaaaggct atcttagtgc tttaagaact ggttggtata ctagtgttat aactatagaa     180
ttaagtaata tcaaggaaaa taagtgtaat ggaacagacg ctaaggcaaa attgataaaa     240
caagaattag ataaatataa aaatgctgta acagaattgc agttgctcat gcaaagcaca     300
ccagcagcca acaatcgagc cagaagagaa ctaccaaggt ttatgaatta tacactcaac     360
aataccaaaa ataacaatgt aacattaagc aagaaaagga aagaagatt tcttggcttt     420 ttgttaggtg ttggatctgc aatcgccagt ggcattgctg tatctaaagt cctgcaccta     480 gaagggaag tgaacaaaat aaaaagtgct ctactatcca caacaaggc tgtagtcagc     540 ttatcaaatg gagttagtgt cttaaccagc aaagtgttag acctcaaaaa ctatatagat     600
aaacagttgt tacccattgt gaacaagcaa agctgcagca tcaaacat tgaaactgtg     660 atagaattcc aacaaaagaa caacagacta ctagagatta ccagggaatt cagtgttaat     720
gcaggtgtaa ctacacctgt aagcacttac atgttaacaa atagtgaatt attatcatta     780
atcaatgata tgcctataac aaatgatcag aaaaatttaa tgtctaacaa tgttcaaata     840
gttagacagc aaagttactc tatcatgtcc ataataaagg aggaagtctt agcatatgta     900
gtacaattac cactatatgg tgtaatagat acaccttgtt ggaaattaca cacatcccct     960
ctatgcacaa ccaacacaaa ggaagggtcc aacatctgtt aacaagaac cgacagagga    1020

```
tggtactgtg acaatgcagg atcagtttct tcttcccac aagctgaaac atgcaaagtt    1080
caatcgaatc gagtattttg tgacacaatg aacagtttaa cattaccaag tgaagtaaac    1140
ctctgcaaca ttgacatatt caaccctaaa tatgattgca aaattatgac ttcaaaaaca    1200
gatgtaagca gctccgttat cacatctcta ggagccattg tgtcatgcta tggcaaaact    1260
aaatgtacag catccaataa aaatcgtgga atcataaaga cattttctaa cgggtgtgat    1320
tatgtatcaa ataagggggt ggacactgta tctgtaggta atacattata ttatgtaaat    1380
aagcaagaag gaaaaagtct ctatgtaaaa ggtgaaccaa taataaattt ctatgaccca    1440
ttagtgttcc cttctgatga atttgatgca tcaatatctc aagtcaatga gaagattaac    1500
cagagcctag catttattcg taatccgat gaattattac ataatgtaaa tgttggtaaa    1560
tccaccacaa atatcatgat aactactata attatagtga ttatagtaat attgttatta    1620
ttaattgcag ttgggctgtt cctatactgc aaggccagaa gcacaccagt cacactaagc    1680
aaggatcaac tgagtggtat aaataatatt gcatttagta ac                      1722
```

<210> SEQ ID NO 18
<211> LENGTH: 574
<212> TYPE: PRT
<213> ORGANISM: Respiratory syncytial virus

<400> SEQUENCE: 18

```
Met Glu Leu Pro Ile Leu Lys Thr Asn Ala Ile Thr Thr Ile Leu Ala
 1               5                  10                  15

Ala Val Leu Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Ala Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Asn Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255
```

-continued

```
Leu Leu Ser Leu Ile Asn Asp Met Pro Ile Thr Asn Asp Gln Lys Asn
            260                 265                 270

Leu Met Ser Asn Asn Val Gln Ile Val Arg Gln Ser Tyr Ser Ile
        275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
                340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
                420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Val Gly Lys Ser Thr Thr Asn Ile Met Ile Thr
        515                 520                 525

Thr Ile Ile Ile Val Ile Ile Val Ile Leu Leu Leu Leu Ile Ala Val
530                 535                 540

Gly Leu Phe Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaaattaaac ctggggcaaa taacc                                          25

<210> SEQ ID NO 20
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 20
acaaaatmaa ctctggggca aataac                                              26

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cttcgygaca tatttgcccc ag                                                  22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggggcamtmc mtggagttgc                                                     20

<210> SEQ ID NO 23
<211> LENGTH: 40
<212> TYPE: PRT
<213> ORGANISM: Respiratory syncytial virus

<400> SEQUENCE: 23

Ala Gly Val Thr Thr Pro Val Ser Thr Tyr Met Leu Thr Asn Ser Glu
1               5                   10                  15

Leu Leu Ser Leu Ile Asn Asp Met Pro Ile Thr Asn Asp Gln Lys Lys
            20                  25                  30

Leu Met Ser Asn Asn Val Gln Ile
        35                  40

<210> SEQ ID NO 24
<211> LENGTH: 40
<212> TYPE: PRT
<213> ORGANISM: Respiratory syncytial virus

<400> SEQUENCE: 24

Ala Gly Val Thr Thr Pro Val Ser Thr Tyr Met Leu Thr Asn Ser Glu
1               5                   10                  15

Leu Leu Ser Leu Ile Asn Asp Met Pro Ile Thr Asn Asp Gln Lys Asn
            20                  25                  30

Leu Met Ser Asn Asn Val Gln Ile
        35                  40

<210> SEQ ID NO 25
<211> LENGTH: 62
<212> TYPE: PRT
<213> ORGANISM: Respiratory syncytial virus

<400> SEQUENCE: 25

Asp Lys Gln Leu Leu Pro Ile Val Asn Lys Gln Ser Cys Ser Ile Ser
1               5                   10                  15
```

```
Asn Ile Glu Thr Val Ile Glu Phe Gln Gln Lys Asn Asn Arg Leu Leu
             20                  25                  30

Glu Ile Thr Arg Glu Phe Ser Val Asn Ala Gly Val Thr Thr Pro Val
         35                  40                  45

Ser Thr Tyr Met Leu Thr Asn Ser Glu Leu Leu Ser Leu Ile
     50                  55                  60

<210> SEQ ID NO 26
<211> LENGTH: 41
<212> TYPE: PRT
<213> ORGANISM: Respiratory syncytial virus

<400> SEQUENCE: 26

Asp Gln Lys Lys Leu Met Ser Asn Asn Val Gln Ile Val Arg Gln Gln
1               5                   10                  15

Ser Tyr Ser Ile Met Ser Ile Ile Lys Glu Glu Val Leu Ala Tyr Val
             20                  25                  30

Val Gln Leu Pro Leu Tyr Gly Val Ile
             35                  40
```

HUMAN MONOCLONAL ANTIBODY SPECIFIC FOR THE F PROTEIN OF RESPIRATORY SYNCYTIAL VIRUS (RSV)

SEQUENCE LISTING

The instant application contains a Sequence Listing which has been submitted electronically in ASCII format and is hereby incorporated by reference in its entirety. Said ASCII copy, created on Nov. 13, 2014, is named 109072-0200_SL.txt and is 17,873 bytes in size.

FIELD OF THE INVENTION

This invention relates to an monoclonal antibody construct or antibody fragment specific for the fusion protein (F protein) of respiratory syncytial virus (RSV), nucleic acids encoding the antibody construct or fragment, and cell lines expressing the antibody construct or fragment. This invention further relates to methods for producing said monoclonal antibody construct or antibody fragment and to the use of said monoclonal antibody construct or antibody fragment for treating or preventing infection by RSV having a normal or mutated version of F protein.

DESCRIPTION OF THE RELATED ART

Respiratory syncytial virus (RSV) is one of the most common causes of respiratory infections in humans, and is the leading cause of infant hospitalization and a leading viral cause of death in infants. RSV epidemics recur annually during the winter season. The severity of outbreaks may vary from year to year due to co-circulation of 2 main RSV strains, group A and B. During a given annual epidemic, a large portion of the population develops RSV upper and/or lower respiratory tract infections.

Approximately two thirds of all infants are infected with RSV during their first year of life. Peak incidence of occurrence is observed at age 2-8 months; by 2 years of age 99% of children have been infected with RSV at least once, and 36% have had at least two infections. Most of these RSV infections cause minor upper respiratory illness and cold-like symptoms. Overall, 4 to 5 million children under 4 years of age acquire an RSV infection, and more than 120,000 children are hospitalized annually in the United States because of this infection.

Attempts at developing an effective vaccine have thus far been unsuccessful. Even upon repeated vaccinations, the human immune system is incapable of raising a sufficiently protective antibody-based immune response. Annually recurring infections are common even among previously infected individuals with normal immune functions, albeit few hospitalizations are seen among older children and adults with intact immune systems. The reasons for the absence of a protective immunity after vaccination or repeated infections are presently unknown. Currently, few treatment options are available for lower respiratory infections with RSV, and treatment must be initiated promptly at the onset of the infection to inhibit the replicating virus effectively. In 1986, the U.S. Food and Drug Administration (FDA) approved ribavirin, a broad-spectrum antiviral agent, for treatment of children with severe RSV disease.

F protein mediates fusion of the viral membrane with the target cell membrane and thus mediates virus genome entry into the target cell. F protein embedded into the membrane of infected cells mediates fusion between infected cells and their neighbors, leading to the syncytia formation characteristic of RSV infection. F protein is a type I fusion protein that rearranges from a metastable pre-fusion conformation to a highly stable post-fusion structure. This structural change in the protein is necessary for membrane fusion. A specific antibody binding to antigenic site II/A may interfere with this structural change, thus preventing infection of the target cell as well as the fusion of infected cells with neighboring cells and the subsequent formation of syncytia.

Inhibition of the fusion mechanism prevents infection in vitro and in vivo, effectively neutralizing the virus. Previous experiments in animals indicated that protection against RSV infection is conferred mainly by neutralizing antibodies, in particular antibodies towards the F protein on the surface of the RSV particle. Rodent-derived monoclonal antibodies, such as MED-493 (also known as palivizumab) were subsequently developed for use in humans at risk for RSV infections (Boeckh, M et al., 2001). Palivizumab was approved by the FDA in 1998 for use in high risk patients, and so far is the only monoclonal antibody directed against RSV that is approved for human use.

A detailed topological and operational map of epitopes involved in neutralization and fusion was constructed using rodent-derived neutralizing antibodies specific for F protein of RSV A2 strain. Three non-overlapping antigenic sites (A, B, and C) and one bridge site (AB) were identified. The commercially available anti-RSV monoclonal antibody, palivizumab, binds to a highly conserved region on the extracellular domain of mature F protein, referred to as antigenic site II or site A (antigenic site II/A), which encompasses amino acids 262 to 275.

The safety and efficacy of palivizumab validate the antigenic site II/A as a crucial and effective target for a monoclonal antibody for use as a prophylactic measure to prevent infections. Nonetheless, a subset of RSV strains are resistant to palivizumab, and use of palivizumab can select for such resistant strains.

A second-generation antibody, motavizumab, was generated by manipulating individual amino acids within the six complementarity determining regions (CDRs) of palivizumab. Amino acids in these regions were individually substituted with any amino acid, and the best combinations for improved potency over palivizumab without changing specificity for the defined epitope were selected. Motavizumab is approximately ten-fold more potent than its predecessor, palivizumab, due to a higher affinity for the F protein. However, motavizumab does not provide significant improvement in protection against RSV infection in patients at high risk for contracting lower respiratory infections and has a higher risk of unwanted side effects, in particular allergic reactions. The FDA did not approve motavizumab for use in humans. As demonstrated by the clinical results, manipulation of a few amino acids in the sequence of an existing antibody can increase the risks for serious side effects in humans.

Therefore, there exists a significant need for novel antibodies that target a broad range of RSV strains, including palivizumab-resistant strains. Furthermore, antibodies that have a lower risk of adverse reactions in humans are of interest.

SUMMARY OF THE INVENTION

This invention is predicated, in part, on the discovery that fully human antibody constructs that recognize the F protein of RSV are able to neutralize both palivizumab-resistant and palivizumab-sensitive RSV strains.

All RSV strains that exhibit resistance to palivizumab have been shown to contain amino acid changes within a specific region in the antigenic region II/A on the F protein (Zhao, X et al., 2004). As an example, palivizumab-resistant RSV strains selected in vitro had mutations at position 272 of the fusion protein, from lysine to asparagine, methionine, threonine, glutamine, or glutamate. Variants containing mutations at positions 272 and 275 were detected in breakthrough patients.

The suitability of the F protein antigenic region II/A as a target for preventing RSV infection, including lower respiratory tract infection, has been confirmed by the efficacy of palivizumab. Although it was previously reported that most epitopes within the antigenic region II/A were constant among subgroup A viruses, several epitopes in site II/A are highly variable among subgroup B viruses. The antigenic site II/A on F protein, and in particular the epitope covered by palivizumab and motavizumab (amino acid positions 262 to 275) is subject to mutations at a frequency of 1 in 20 of all clinical isolates tested. Palivizumab is ineffective at preventing lower respiratory tract infections by these mutant strains. Thus, antibodies targeting the same antigenic region might exhibit improved efficacy as compared to palivizumab and motavizumab in cases where mutations are found in these amino acid positions. Therefore, an urgent need exists to develop novel monoclonal antibodies that bind to the antigenic region II/A of RSV F protein with higher affinity than palivizumab and that are capable of preventing and/or treating infection by palivizumab-resistant RSV strains.

Severe allergic reactions are common side effects of antibody-based preventive and/or therapeutic interventions, significantly limiting the use of such antibodies. Severe allergic side effects have been observed during the clinical testing of motavizumab. For example, an increased frequency of hypersensitivity reactions, including cases suggestive of anaphylaxis, was observed in clinical testing. Several patients treated with multiple doses of motavizumab developed anti-drug antibodies (ADA) and had severe allergic reactions due to ADA. Both palivizumab and motavizumab are mouse derived and not of human origin. Motavizumab's de novo-designed amino acid structure at the CDRs and its residual murine sequences are possible reasons for adverse reactions in late stage clinical studies, and motavizumab was ultimately deemed not safe for human use.

Antibodies generated by the human immune system against pathogens such as RSV inherently exhibit lower propensity to react with human self-antigens. In a preferred embodiment, the novel antibody constructs or antibody fragments targeting RSV described herein are entirely constructed from human origin.

Palivizumab is not sufficient to prevent infection by every RSV isolate. Therefore, a fully human, high-affinity antibody construct or antibody fragment with specificity to an RSV antigenic region (such as II/A) is highly desired. In one embodiment, the antibody construct or antibody fragment preferably recognizes both palivizumab-sensitive and palivizumab-resistant RSV strains. In one embodiment, the antibody construct or antibody fragment preferably has an affinity constant of greater than about $10^{-9}$ M, and preferably greater than about $10^{-10}$ M, or greater than about $10^{-11}$ M. In one embodiment, the antibody construct or antibody fragment recognizes and neutralizes human RSV strains of type A and B. In one embodiment, the antibody construct or antibody fragment recognizes and neutralizes more than one RSV strain, and preferably at least one palivizumab-resistant RSV strain.

In one embodiment of the present invention, a fully human antibody construct or fragment thereof with specificity to RSV antigenic region II/A and an affinity constant of at least $10^{-9}$ M, and preferably greater than $10^{-10}$ M, is described. In another embodiment, the fully human antibody construct or fragment thereof is capable of neutralizing RSV virus strains of type A and B. In one embodiment, the antibody is capable of inhibiting binding by palivizumab. In one embodiment, the antibody construct or antibody fragment neutralizes at least one palivizumab-resistant strain.

In one embodiment, the invention relates to a cell comprising one or more cDNA sequences which encode a heavy chain variable region and/or a light chain variable region, wherein each cDNA sequence is constructed from an RSV-infected human, which cell produces an antibody construct or antibody fragment comprising the heavy chain variable region and/or the light chain variable region, such that the antibody construct or fragment thereof binds to RSV antigenic region II/A. In a preferred embodiment, the antibody construct or antibody fragment binds to RSV antigenic region II/A with an affinity of greater than $1\times10^{-9}$ M. In one embodiment, the cell is a eukaryotic cell. In one embodiment, the cell is a mammalian cell. In one embodiment, the cell is a plant cell. In one embodiment, the cell is a HEK293T cell. In one embodiment, the cell is a tobacco cell.

In one embodiment, the heavy chain variable region cDNA sequence is coupled to a cDNA sequence which encodes a constant region of human immunoglobulin. In a preferred embodiment, the constant region cDNA sequence is from a different patient than the heavy chain variable region and/or the light chain variable region. In one embodiment, the human immunoglobulin is from IgG1.

In one embodiment, the heavy chain variable region cDNA sequence comprises a nucleotide sequence having at least 90% sequence homology to the nucleotide sequence of SEQ ID NO.:2. In one embodiment, the nucleotide sequence encoding a complementarity determining region (CDR)1 of the heavy chain of the antibody construct or antibody fragment comprises a nucleotide sequence having at least 90% sequence homology to the nucleotide sequence of SEQ ID NO.: 5. In one embodiment, the nucleotide sequence encoding CDR2 of the heavy chain of the antibody construct or antibody fragment comprises a nucleotide sequence having at least 90% sequence homology to the nucleotide sequence of SEQ ID NO.: 6. In one embodiment, the nucleotide sequence encoding CDR3 of the heavy chain of the antibody construct or antibody fragment comprises a nucleotide sequence having at least 90% sequence homology to the nucleotide sequence of SEQ ID NO.: 7.

In one embodiment, the light chain variable region cDNA sequence is coupled to a cDNA sequence which encodes a light chain constant region of human immunoglobulin. In a preferred embodiment, the constant region cDNA sequence is from a different patient than the light chain variable region and/or the heavy chain variable region. In one embodiment, the human immunoglobulin is from IgG1.

In one embodiment, the light chain variable region cDNA sequence comprises a nucleotide sequence having at least 90% sequence homology to the nucleotide sequence of SEQ ID NO.:4. In one embodiment, the nucleotide sequence encoding CDR1 of the light chain of the antibody construct or antibody fragment comprises a nucleotide sequence having at least 90% sequence homology to the nucleotide sequence of SEQ ID NO.: 11. In one embodiment, the nucleotide sequence encoding CDR2 of the light chain of the antibody construct or antibody fragment comprises a nucleotide sequence having at least 90% sequence homology to the nucleotide sequence of SEQ ID NO.: 12. In one embodiment, the nucleotide sequence encoding CDR3 of the light chain of the antibody construct or antibody fragment comprises a nucleotide sequence having at least 90% sequence homology to the nucleotide sequence of SEQ ID NO.: 13.

In one embodiment, this invention relates to a cDNA sequence as described herein. In one embodiment, this invention relates to an RNA molecule encoded by a cDNA sequence as described herein.

In one embodiment, this invention is directed to an antibody construct or antibody fragment that binds to RSV antigenic region II/A. In a preferred embodiment, the antibody construct or antibody fragment binds to RSV antigenic region II/A with an affinity of greater than $1 \times 10^{-9}$. In one embodiment, the antibody construct or antibody fragment is capable of neutralizing at least one RSV strain. In a preferred embodiment, the antibody construct or antibody fragment is capable of neutralizing at least one RSV strain that is resistant to palivizumab. In one embodiment, the neutralization capacity of the antibody construct or antibody fragment against at least one RSV strain is at least 2 times greater than the neutralization capacity of palivizumab. In one embodiment, the neutralization capacity of the antibody construct or antibody fragment against at least one RSV strain is at least 3 times greater than the neutralization capacity of palivizumab. In one embodiment, the neutralization capacity of the antibody construct or antibody fragment against at least one RSV strain is at least 4 times greater than the neutralization capacity of palivizumab. In one embodiment, the neutralization capacity of the antibody construct or antibody fragment against at least one RSV strain is at least 5 times greater than the neutralization capacity of palivizumab. In one embodiment, the neutralization capacity of the antibody construct or antibody fragment against at least one RSV strain is at least 10 times greater than the neutralization capacity of palivizumab. In one embodiment, the neutralization capacity of the antibody construct or antibody fragment against at least one RSV strain is at least 15 times greater than the neutralization capacity of palivizumab.

In one embodiment, the heavy chain variable region of the antibody construct or antibody fragment comprises an amino acid sequence having at least 90% sequence homology to the amino acid sequence of SEQ ID NO.: 1. In one embodiment, the amino acid sequence of CDR1 of the heavy chain of the antibody construct or antibody fragment comprises an amino acid sequence having at least 90% sequence homology to GASINLYD (SEQ ID NO.:8). In one embodiment, the amino acid sequence of CDR2 of the heavy chain of the antibody construct or antibody fragment comprises an amino acid sequence having at least 90% sequence homology to GYISGST (SEQ ID NO.:9). In one embodiment, the amino acid sequence of CDR3 of the heavy chain of the antibody construct or antibody fragment comprises an amino acid sequence having at least 90% sequence homology to ARDVGWGPQYYYGLDV (SEQ ID NO.:10).

In one embodiment, the light chain variable region of the antibody construct or antibody fragment comprises an amino acid sequence having at least 90% sequence homology to the amino acid sequence of SEQ ID NO.: 3. In one embodiment, the amino acid sequence of CDR1 of the light chain of the antibody construct or antibody fragment comprises an amino acid sequence having at least 90% sequence homology to HSVQSTS (SEQ ID NO.:14). In one embodiment, the amino acid sequence of CDR2 of the light chain of the antibody construct or antibody fragment comprises an amino acid sequence having at least 90% sequence homology to GGS (SEQ ID NO.:15). In one embodiment, the amino acid sequence of CDR3 of the light chain of the antibody construct or antibody fragment comprises an amino acid sequence having at least 90% sequence homology to QQSDRSPPIT (SEQ ID NO.:16).

In one embodiment, the antibody construct or antibody fragment recognizes an epitope on the F protein of RSV. In one embodiment, the antibody construct or antibody fragment recognizes an epitope within the antigenic region II/A of the RSV F protein. In one embodiment, the antibody construct or antibody fragment recognizes an amino acid sequence having at least 90% sequence homology to the epitope of SEQ ID NO.:23 and/or SEQ ID NO.: 24.

In a preferred embodiment, the antibody construct or fragment is fully human. In one embodiment, the antibody construct or antibody fragment is chimeric. In one embodiment, the antibody construct or antibody fragment is humanized.

In one embodiment, the antibody construct or antibody fragment comprises (a) a heavy chain complementarity determining region (CDR)1 comprising the amino acid sequence GASINLYD (SEQ ID NO.:8); (b) a heavy chain CDR2 comprising the amino acid sequence GYISGST (SEQ ID NO.:9); (c) a heavy chain CDR3 comprising the amino acid sequence ARDVGWGPQYYYGLDV (SEQ ID NO.:10); (d) a light chain CDR1 comprising the amino acid sequence HSVQSTS (SEQ ID NO.:14), (e) a light chain CDR2 comprising the amino acid sequence GGS (SEQ ID NO.:15), and (f) a light chain CDR3 comprising the amino acid sequence QQSDRSPPIT (SEQ ID NO.:16).

In one embodiment, this invention relates to a pharmaceutical composition comprising an antibody construct or antibody fragment as described herein and a pharmaceutically acceptable carrier, diluent, or excipient. In one embodiment, the antibody construct or antibody fragment is lyophilized. In one embodiment, the antibody construct or antibody fragment is in an aqueous solution. In one embodiment, this invention relates to a bag for intravenous therapy, comprising the antibody construct or antibody fragment as described herein and a pharmaceutically acceptable carrier, diluent, or excipient.

In one embodiment, this invention relates to a method of producing an antibody construct or functional part thereof, the method comprising culturing a cell as described above under conditions in which the cDNA sequences are expressed, thereby producing an antibody construct or fragment that binds with specificity to RSV antigenic region II/A. In a preferred embodiment, the antibody or a fragment thereof bind to RSV antigenic region II/A with an affinity of greater than $1 \times 10^{-9}$. In a further preferred embodiment, the antibody or fragment thereof is capable of neutralizing at least one RSV strain. In an especially preferred embodiment, the antibody or fragment thereof is capable of neutralizing at least one RSV strain that is resistant to palivizumab.

In one embodiment, this invention relates to a chromatography column or membrane comprising an antibody construct or antibody fragment as described herein, wherein the antibody construct or antibody fragment is bound to the chromatography column or membrane. In one embodiment, the chromatography column or membrane comprises Protein A, e.g. a Protein A resin. In one embodiment, the chromatography column or membrane comprises an ion exchange resin. In one embodiment, the chromatography column or membrane comprises a hydrophobic charge induction chromatography column.

In one aspect, this invention relates to a method for treating a patient infected with RSV by administering an antibody construct or antibody fragment as described herein to the patient. In one aspect, this invention relates to a method for preventing infection by RSV in a patient at risk for RSV infection by administering an antibody construct or antibody fragment as described herein to the patient. Administration may be by any suitable method, as determined by a skilled clinician. In a preferred embodiment, the antibody construct or antibody fragment is administered by intramuscular or intravenous administration.

BRIEF DESCRIPTION OF THE DRAWINGS

FIG. 1 is a schematic of the process used to isolate an antibody specific for RSV F protein from selected and cultured human lymphocytes.

FIG. 2 describes the complete nucleotide sequence (SEQ ID NO.: 1) and the amino acid sequence (SEQ ID NO.: 2) of the variable region of the heavy chain of AR201.

FIG. 3 describes the complete nucleotide sequence (SEQ ID NO.: 3) and the amino acid sequence (SEQ ID NO.: 4) of the variable region of the kappa light chain of AR201.

FIG. 4 describes the complete nucleotide sequences (SEQ ID NO.: 5; SEQ ID NO.: 6; SEQ ID NO.: 7) and the amino acid sequences (SEQ ID NO.: 8; SEQ ID NO.: 9; SEQ ID NO.: 10) of the CDR regions of the variable region of the heavy chain of AR201.

FIG. 9A provides the nucleotide sequence (SEQ ID NO.: 17) of the F protein of a clinical isolate that is resistant to palivizumab.

FIG. 9B describes the amino acid sequence (SEQ ID NO.: 18) of the F protein of one clinical isolate resistant to palivizumab.

FIG. 10 provides the amino acid sequence of the palivizumab epitope (SEQ ID NO.: 23), and the corresponding amino acid sequence of the F protein of a palivizumab-resistant strain (SEQ ID NO.: 24) that is recognized by AR201.

FIG. 11 provides the predicted peptides (SEQ ID NO.: 25 and SEQ ID NO.: 26) resulting from Asp-N digestion of RSV F protein that contain fragments of the palivizumab epitope.

FIG. 12 describes Asp-N cleavage of RSV F protein that is bound by AR201 (black bars) or palivizumab (white bars).

DETAILED DESCRIPTION

Figures 5, 6:
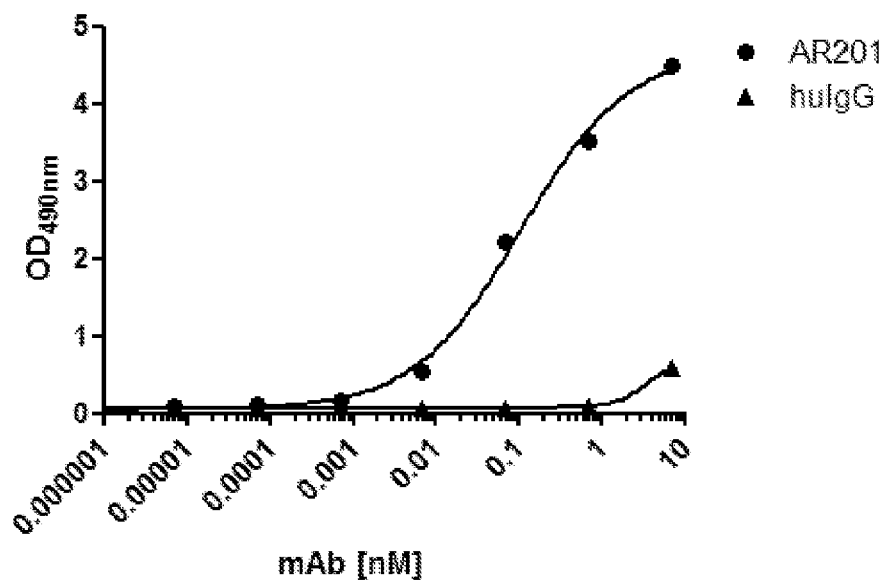
FIG. 5 describes the complete nucleotide sequences (SEQ ID NO.: 11; SEQ ID NO.: 12; SEQ ID NO.: 13) and the amino acid sequences (SEQ ID NO.: 14; SEQ ID NO.: 15; SEQ ID NO.: 16) of the CDR regions of the variable region of the light chain of AR201.
FIG. 6 describes the binding of purified AR201 (●) and human non-specific monoclonal IgG1 (▲) to RSV-EIA antigen over a broad range of concentrations.

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a compound" includes a plurality of compounds.

I. Definitions

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 10%, 5% or 1%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

"Pharmaceutically acceptable composition" refers to a composition that is suitable for administration to a human. Such compositions include various excipients, diluents, carriers, and such other inactive agents well known to the skilled artisan.

"Therapeutically effective amount" or "therapeutic amount" refers to an amount of a drug or an agent that, when administered to a patient suffering from a condition, will have the intended therapeutic effect, e.g., alleviation, amelioration, palliation or elimination of one or more manifestations of the condition in the patient. The therapeutically effective amount will vary depending upon the patient and the condition being treated, the weight and age of the subject, the severity of the condition, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations.

"Treatment," "treating," and "treat" are defined as acting upon a disease, disorder, or condition with an agent to reduce or ameliorate harmful or any other undesired effects of the disease, disorder, or condition and/or its symptoms. "Treatment," as used herein, covers the treatment of a patient, and includes: (a) reducing the risk of occurrence of the condition in a patient determined to be predisposed to the condition but not yet diagnosed as having the condition, (b) impeding the development of the condition, and/or (c) relieving the condition, i.e., causing regression of the condition and/or relieving one or more symptoms of the condition. "Treating" or "treatment of" a condition or patient refers to taking steps to obtain beneficial or desired results, including clinical results such as the reduction of symptoms. For purposes of this invention, beneficial or desired clinical results include, but are not limited to: preventing infection of a patient at risk of RSV infection; or reducing the severity of infection by RSV, e.g., by reducing one or more symptoms, reducing the length of time of infection, etc.

As used herein, the term "patient" refers to a mammal. In a preferred embodiment, the patient is a human.

As used herein, the term "strain" or "RSV strain" refers to any RSV. Strains include, but are not limited to, clinical isolates, variants, mutants, and the like. Strains may be palivizumab-resistant or palivizumab-sensitive. Strains may be of either RSV type, A or B. general, strains are distinguishable by one or more genetic mutations, even if such mutation does not confer a different characteristic to the virus.

As used herein, the term "antibody construct" refers to an antibody wherein at least a portion of the antibody is derived from an antibody from a human patient who had been exposed to the antigen of interest. An antibody construct may be an entire antibody or a fragment or portion thereof, provided the antibody, fragment, or portion has the recited affinity for F protein. An antibody construct may be fully human, humanized, or chimeric. An antibody construct may comprise amino acid sequences derived from a single patient, multiple patients, and/or known antibody sequences (e.g., a consensus constant region sequence).

As used herein, the term "antibody fragment" refers to any portion of the antibody that recognizes an epitope. Antibody fragments may be glycosylated. By way of non-limiting example, the antibody fragment may be a Fab fragment, a Fab' fragment, a F(ab')2 fragment, a Fv fragment, a r IgG fragment, a functional antibody fragment, single chain recombinant forms of the foregoing, and the like. F(ab')2, Fab, Fab' and Fv are antigen-binding fragments that can be generated from the variable region of IgG and IgM. They vary in size, valency, and Fc content. The fragments may be generated by any method, including expression of the constituents (e.g., heavy and light chain portions) by a cell or cell line, or multiple cells or cell lines.

"F(ab')2" fragments contain two antigen-binding regions joined at the hinge through disulfide linkages and lack most of the Fc region. "Fab'" fragments are derived from F(ab')2 but include only one antigen binding region. They may contain a small portion of Fc.

"Fab" fragments are monovalent fragments produced from IgG and IgM, consisting of the variable heavy chain, constant heavy chain, and variable light chain, constant light chain regions, linked by an intramolecular disulfide bond.

"Fv" is the smallest fragment produced from IgG and IgM that contains a complete antigen-binding site. Fv comprises a portion of the variable heavy and light chains, held together by non-covalent interactions. These chains tend to dissociate upon dilution, but can be cross-linked, for example using glutaraldehyde, intermolecular disulfides or a peptide linker. Fv fragments have the same binding properties and similar three-dimensional binding characteristics as Fab.

"rIgG" refers to reduced IgG or half-IgG, containing one heavy chain and one light chain. rIgG can be produced by selectively reducing the hinge-region disulfide bonds.

As used herein, the term "fully human antibody" refers to an antibody, antibody construct, or antibody fragment consisting entirely of human amino acid sequence. That is, the amino acid sequence of the human monoclonal antibody construct is derived from a human cell. This may be obtained in different ways. For example, the human monoclonal antibody construct consisting of human amino acid sequence can be obtained from a cell engineered to express the variable region heavy and light chains and/or CDRs from an antibody derived from a human patient (e.g., a patient who had been exposed to RSV and/or RSV F protein). Alternatively, the human monoclonal antibody construct can be obtained from a hybridoma, wherein the B-cell is a human B-cell. Alternatively, the human monoclonal antibody construct may be obtained by CDR grafting of the CDR regions, for example those indicated in FIGS. 4 and 5, onto available human monoclonal antibodies, thereby producing a human monoclonal antibody construct in accordance with the present invention. The entirely human amino acid sequence of the human monoclonal antibody construct prevents the occurrence of undesired adverse effects such as rejection reactions or anaphylactic shock.

The term "neutralizing" or "neutralizing capacity" as used herein refers to the ability of the antibody construct to attenuate infectivity by the virus. For example, the antibody construct may render the viral fusion protein ineffective such that the fusion between the virus and a cell, and/or between infected cells, is blocked or attenuated. An antibody having at least twice the neutralizing capacity of palivizumab is set forth herein, as shown in Example 6 (as determined by infectivity assay).

Monoclonal Antibody Constructs and Fragments Thereof

The current invention relates to a monoclonal antibody construct or antibody fragment that specifically binds the RSV F protein. Preferably, the antibody construct or antibody fragment specifically binds to the F protein antigenic region II/A.

In one embodiment, the antibody construct or antibody fragment binds to F protein with an affinity of greater than $1 \times 10^{-9}$ M. In one embodiment, the antibody construct or antibody fragment binds to F protein with an affinity of greater than $1 \times 10^{-10}$ M. In one embodiment, the antibody construct or antibody fragment binds to F protein with an affinity of greater than $5 \times 10^{-10}$ M. In one embodiment, the antibody construct or antibody fragment binds to F protein with an affinity of greater than $1 \times 10^{-11}$ M. In one embodiment, the antibody construct or antibody fragment binds to F protein with an affinity of greater than $1 \times 10^{-12}$ M. In one embodiment, the antibody construct or antibody fragment binds to F protein with an affinity of greater than $5 \times 10^{-12}$ M.

In one embodiment, the antibody construct or antibody fragment binds to F protein with a higher affinity than palivizumab. In one embodiment, the antibody construct or antibody fragment binds to F protein with an affinity of between about 2:1 and about 500:1 versus palivizumab. In a preferred embodiment, the antibody construct or antibody fragment binds to F protein with an affinity of between about 20:1 and about 200:1 versus palivizumab. It is to be understood that the ratio can be ranges between any two of these values, or any value there between (including endpoints). In one embodiment, the antibody construct or antibody fragment binds to F protein with an affinity of at least about 2:1 versus palivizumab. In one embodiment, the antibody construct or antibody fragment binds to F protein with an affinity of at least about 5:1 versus palivizumab. In one embodiment, the antibody construct or antibody fragment binds to F protein with an affinity of at least about 10:1 versus palivizumab. In one embodiment, the antibody construct or antibody fragment binds to F protein with an affinity of at least about 50:1 versus palivizumab. In one embodiment, the antibody construct or antibody fragment binds to F protein with an affinity of at least about 100:1 versus palivizumab. In one embodiment, the antibody construct or antibody fragment binds to F protein with an affinity of at least about 200:1 versus palivizumab. In one embodiment, the antibody construct or antibody fragment binds to F protein with an affinity of at least about 300:1 versus palivizumab. In one embodiment, the antibody construct or antibody fragment binds to F protein with an affinity of at least about 400:1 versus palivizumab. In one embodiment, the antibody construct or antibody fragment binds to F protein with an affinity of at least about 500:1 versus palivizumab.

In one aspect, the antibody construct or antibody fragment is capable of neutralizing RSV virus strains. In one embodiment, the antibody construct or antibody fragment is capable of neutralizing at least one RSV strain. In one embodiment, the antibody construct or antibody fragment is capable of neutralizing at least one RSV type A strain. In one embodiment, the antibody construct or antibody fragment is capable of neutralizing at least one RSV type B strain. In a preferred embodiment, the antibody construct or antibody fragment is capable of neutralizing at least one RSV type A strain and at least one type B strain. In an especially preferred embodiment, the antibody construct or antibody fragment is capable of neutralizing at least one strain that is resistant to palivizumab.

In one embodiment, the antibody construct or antibody fragment is capable of neutralizing at least one RSV strain with a greater neutralization capacity than palivizumab. In one embodiment, the neutralization capacity of the antibody construct or antibody fragment against at least one RSV strain is at least two times greater than the neutralization capacity of palivizumab. In one embodiment, the neutralization capacity of the antibody construct or antibody fragment against at least one RSV strain is at least five times greater than the neutralization capacity of palivizumab. In one embodiment, the neutralization capacity of the antibody construct or antibody fragment against at least one RSV strain is at least ten times greater than the neutralization capacity of palivizumab. In one embodiment, the neutralization capacity of the antibody construct or antibody fragment against at least one RSV strain is at least fifteen times greater than the neutralization capacity of palivizumab.

In one aspect, the antibody construct or antibody fragment comprises an amino acid sequence having at least 85% sequence homology to the amino acid sequence of SEQ ID NO.: 1. In one embodiment, the antibody construct or antibody fragment comprises an amino acid sequence having at least 90% sequence homology to the amino acid sequence of SEQ ID NO.: 1. In one embodiment, the antibody construct or antibody fragment comprises an amino acid sequence having at least 95% sequence homology to the amino acid sequence of SEQ ID NO.: 1. In one embodiment, the antibody construct or antibody fragment comprises an amino acid sequence having at least 96% sequence homology to the amino acid sequence of SEQ ID NO.: 1. In one embodiment, the antibody construct or antibody fragment comprises an amino acid sequence having at least 97% sequence homology to the amino acid sequence of SEQ ID NO.: 1. In one embodiment, the antibody construct or antibody fragment comprises an amino acid sequence having at least 98% sequence homology to the amino acid sequence of SEQ ID NO.: 1. In one embodiment, the antibody construct or antibody fragment comprises an amino acid sequence having at least 99% sequence homology to the amino acid sequence of SEQ ID NO.: 1. In one embodiment, the antibody construct or antibody fragment comprises the amino acid sequence of SEQ ID NO.: 1. In a preferred embodiment, the heavy chain variable region of the antibody construct or antibody fragment comprises the amino acid sequence of SEQ ID NO.: 1.

In one aspect, the antibody construct or antibody fragment comprises at least one CDR with an amino acid sequence having at least 85% sequence homology to the amino acid sequence of SEQ ID NO.: 8, SEQ ID NO.: 9, and/or SEQ ID NO.: 10. In one embodiment, the antibody construct or antibody fragment comprises at least one CDR with an amino acid sequence having at least 90% sequence homology to the amino acid sequence of SEQ ID NO.: 8, SEQ ID NO.: 9, and/or SEQ ID NO.: 10. In one embodiment, the antibody construct or antibody fragment comprises at least one CDR with an amino acid sequence having at least 95% sequence homology to the amino acid sequence of SEQ ID NO.: 8, SEQ ID NO.: 9, and/or SEQ ID NO.: 10. In one embodiment, the antibody construct or antibody fragment comprises at least one CDR with an amino acid sequence having at least 96% sequence homology to the amino acid sequence of SEQ ID NO.: 8, SEQ ID NO.: 9, and/or SEQ ID NO.: 10. In one embodiment, the antibody construct or antibody fragment comprises at least one CDR with an amino acid sequence having at least 97% sequence homology to the amino acid sequence of SEQ ID NO.: 8, SEQ ID NO.: 9, and/or SEQ ID NO.: 10. In one embodiment, the antibody construct or antibody fragment comprises at least one CDR with an amino acid sequence having at least 98% sequence homology to the amino acid sequence of SEQ ID NO.: 8, SEQ ID NO.: 9, and/or SEQ ID NO.: 10. In one embodiment, the antibody construct or antibody fragment comprises at least one CDR with an amino acid sequence having at least 99% sequence homology to the amino acid sequence of SEQ ID NO.: 8, SEQ ID NO.: 9, and/or SEQ ID NO.: 10. In one embodiment, the antibody construct or antibody fragment comprises at least one CDR with the amino acid sequence of SEQ ID NO.: 8, SEQ ID NO.: 9, and/or SEQ ID NO.: 10. In a preferred embodiment, the antibody construct or antibody fragment comprises a heavy chain CDR1 with the amino acid sequence of SEQ ID NO.: 8, a heavy chain CDR2 with the amino acid sequence of SEQ ID NO.: 9, and a heavy chain CDR3 with the amino acid sequence of SEQ ID NO.: 10.

In one aspect, the antibody construct or antibody fragment comprises an amino acid sequence having at least 85% sequence homology to the amino acid sequence of SEQ ID NO.: 3. In one embodiment, the antibody construct or antibody fragment comprises an amino acid sequence having at least 90% sequence homology to the amino acid sequence of SEQ ID NO.: 3. In one embodiment, the antibody construct or antibody fragment comprises an amino acid sequence having at least 95% sequence homology to the amino acid sequence of SEQ ID NO.: 3. In one embodiment, the antibody construct or antibody fragment comprises an amino acid sequence having at least 96% sequence homology to the amino acid sequence of SEQ ID NO.: 3. In one embodiment, the antibody construct or antibody fragment comprises an amino acid sequence having at least 97% sequence homology to the amino acid sequence of SEQ ID NO.: 3. In one embodiment, the antibody construct or antibody fragment comprises an amino acid sequence having at least 98% sequence homology to the amino acid sequence of SEQ ID NO.: 3. In one embodiment, the antibody construct or antibody fragment comprises an amino acid sequence having at least 99% sequence homology to the amino acid sequence of SEQ ID NO.: 3. In one embodiment, the antibody construct or antibody fragment comprises the amino acid sequence of SEQ ID NO.: 3. In a preferred embodiment, the light chain variable region of the antibody construct or antibody fragment comprises the amino acid sequence of SEQ ID NO.: 3.

In one aspect, the antibody construct or antibody fragment comprises at least one CDR with an amino acid sequence having at least 85% sequence homology to the amino acid sequence of SEQ ID NO.: 14, SEQ ID NO.: 15, and/or SEQ ID NO.: 16. In one embodiment, the antibody construct or antibody fragment comprises at least one CDR with an amino acid sequence having at least 90% sequence homology to the amino acid sequence of SEQ ID NO.: 14, SEQ ID NO.: 15, and/or SEQ ID NO.: 16. In one embodiment, the antibody construct or antibody fragment comprises at least one CDR with an amino acid sequence having at least 95% sequence homology to the amino acid sequence of SEQ ID NO.: 14, SEQ ID NO.: 15, and/or SEQ ID NO.: 16. In one embodiment, the antibody construct or antibody fragment comprises at least one CDR with an amino acid sequence having at least 96% sequence homology to the amino acid sequence of SEQ ID NO.: 14, SEQ ID NO.: 15, and/or SEQ ID NO.: 16. In one embodiment, the antibody construct or antibody fragment comprises at least one CDR with an amino acid sequence having at least 97% sequence homology to the amino acid sequence of SEQ ID NO.: 14, SEQ ID NO.: 15, and/or SEQ ID NO.: 16. In one embodiment, the antibody construct or antibody fragment comprises at least one CDR with an amino acid sequence having at least 98% sequence homology to the amino acid sequence of SEQ ID NO.: 14, SEQ ID NO.: 15, and/or SEQ ID NO.: 16. In one embodiment, the antibody construct or antibody fragment comprises at least one CDR with an amino acid sequence having at least 99% sequence homology to the amino acid sequence of SEQ ID NO.: 14, SEQ ID NO.: 15, and/or SEQ ID NO.: 16. In one embodiment, the antibody construct or antibody fragment comprises at least one CDR with the amino acid sequence of SEQ ID NO.: 14, SEQ ID NO.: 15, and/or SEQ ID NO.: 16. In a preferred embodiment, the antibody construct or antibody fragment comprises a light chain CDR1 with the amino acid sequence of SEQ ID NO.: 14, a light chain CDR2 with the amino acid sequence of SEQ ID NO.: 15, and a light chain CDR3 with the amino acid sequence of SEQ ID NO.: 16.

The invention further relates to derivatives of the antibody construct or antibody fragment described herein. The term "derivative" encompasses any mutants of the antibody construct differing by the addition, deletion, and/or substitution of at least one amino acid. Preferably, the derivative is a mutant of the antibody construct that carries at least one conservative substitution in any of the CDRs in the heavy chain and/or light chain as indicated in FIGS. 4 and 5. More preferably, the mutant has not more than 5, not more than 4, preferably not more than 3, particularly preferred not more than 2 conservative substitutions. The capacity of the fragment or derivative of the antibody to bind to the epitope can be determined by direct ELISA, for example, as described in the Examples section below.

In accordance with the present invention, the term "conservative substitution" means a replacement of one amino acid belonging to a particular physico-chemical group with an amino acid belonging to the same physico-chemical group. The physico-chemical groups are defined as follows: The group of non-polar amino acids comprises: glycine, alanine, valine, leucine, isoleucine, methionine, proline, phenylalanine, and tryptophan. The group of amino acids having uncharged polar side chains comprises asparagine, glutamine, tyrosine, cysteine, and cysteine. The physico-chemical group of amino acids having a positively charged polar side chain comprises lysine, arginine, and histidine. The physico-chemical group of amino acids having a negatively charged polar side chain comprises aspartic acid and glutamic acid, also referred to as aspartate and glutamate.

In one embodiment, the light chain of the antibody construct or antibody fragment according to the present invention is of the kappa or lambda type. In a preferred embodiment, the light chain is of the kappa type. The light chain may be either a naturally occurring chain including a naturally rearranged, a genetically modified or synthetic type of light chain. According to a further embodiment, the heavy chain of the antibody of the present invention is selected from all human isotypes, namely IgM, IgA, or IgG. The light chain and heavy chain may either be covalently linked as a single-chain antibody (e. g. bivalent scFv, bifunctional scFv and bispecific scFv) or non-covalently linked with each other.

In one aspect, the antibody construct or antibody fragment recognizes an epitope on the F protein of RSV. In one embodiment, the epitope is within antigenic region II/A. In one embodiment, the antibody construct recognizes an epitope within antigenic region II/A having at least 85% sequence homology to a portion of the amino acid sequence of SEQ ID NO.: 23 or SEQ ID NO.: 24. In one embodiment, the antibody construct recognizes an epitope within antigenic region II/A having at least 90% sequence homology to a portion of the amino acid sequence of SEQ ID NO.: 23 or SEQ ID NO.: 24. In one embodiment, the antibody construct recognizes an epitope within antigenic region II/A having at least 95% sequence homology to a portion of the amino acid sequence of SEQ ID NO.: 23 or SEQ ID NO.: 24. In one embodiment, the antibody construct recognizes an epitope within antigenic region II/A having at least sequence 96% homology to a portion of the amino acid sequence of SEQ ID NO.: 23 or SEQ ID NO.: 24. In one embodiment, the antibody construct recognizes an epitope within antigenic region II/A having at least 97% sequence homology to a portion of the amino acid sequence of SEQ ID NO.: 23 or SEQ ID NO.: 24. In one embodiment, the antibody construct recognizes an epitope within antigenic region II/A having at least 98% sequence homology to a portion of the amino acid sequence of SEQ ID NO.: 23 or SEQ ID NO.: 24. In one embodiment, the antibody construct recognizes an epitope within antigenic region II/A having at least 99% sequence homology to a portion of the amino acid sequence of SEQ ID NO.: 23 or SEQ ID NO.: 24.

In one embodiment, the antibody construct recognizes an epitope within antigenic region II/A having at least 85% sequence homology to a portion of the amino acid sequence of SEQ ID NO.: 25 or SEQ ID NO.: 26. In one embodiment, the antibody construct recognizes an epitope within antigenic region II/A having at least 90% sequence homology to a portion of the amino acid sequence of SEQ ID NO.: 25 or SEQ ID NO.: 26. In one embodiment, the antibody construct recognizes an epitope within antigenic region II/A having at least 95% sequence homology to a portion of the amino acid sequence of SEQ ID NO.: 25 or SEQ ID NO.: 26. In one embodiment, the antibody construct recognizes an epitope within antigenic region II/A having at least sequence 96% homology to a portion of the amino acid sequence of SEQ ID NO.: 25 or SEQ ID NO.: 26. In one embodiment, the antibody construct recognizes an epitope within antigenic region II/A having at least 97% sequence homology to a portion of the amino acid sequence of SEQ ID NO.: 25 or SEQ ID NO.: 26. In one embodiment, the antibody construct recognizes an epitope within antigenic region II/A having at least 98% sequence homology to a portion of the amino acid sequence of SEQ ID NO.: 25 or SEQ ID NO.: 26. In one embodiment, the antibody construct recognizes an epitope within antigenic region II/A having at least 99% sequence homology to a portion of the amino acid sequence of SEQ ID NO.: 26 or SEQ ID NO.: 26.

The present invention further relates to nucleotide sequences encoding the antibody construct or antibody fragment, or portions thereof. In one embodiment, the nucleotide sequence comprises a cDNA sequence. In one embodiment, the nucleotide sequence comprises a cDNA sequence encoding for the heavy chain variable region. In one embodiment, the cDNA sequence encoding for the heavy chain variable region has at least 85% sequence homology to the nucleotide sequence of SEQ ID NO.: 2. In one embodiment, the cDNA sequence encoding for the heavy chain variable region has at least 90% sequence homology to the nucleotide sequence of SEQ ID NO.: 2. In one embodiment, the cDNA sequence encoding for the heavy chain variable region has at least 95% sequence homology to the nucleotide sequence of SEQ ID NO.: 2. In one embodiment, the cDNA sequence encoding for the heavy chain variable region has at least 96% sequence homology to the nucleotide sequence of SEQ ID NO.: 2. In one embodiment, the cDNA sequence encoding for the heavy chain variable region has at least 97% sequence homology to the nucleotide sequence of SEQ ID NO.: 2. In one embodiment, the cDNA sequence encoding for the heavy chain variable region has at least 98% sequence homology to the nucleotide sequence of SEQ ID NO.: 2. In one embodiment, the cDNA sequence encoding for the heavy chain variable region has at least 99% sequence homology to the nucleotide sequence of SEQ ID NO.: 2.

In one embodiment, the nucleotide sequence comprises a cDNA sequence encoding for the light chain variable region. In one embodiment, the cDNA sequence encoding for the light chain variable region has at least 85% sequence homology to the nucleotide sequence of SEQ ID NO.: 4. In one embodiment, the cDNA sequence encoding for the light chain variable region has at least 90% sequence homology to the nucleotide sequence of SEQ ID NO.: 4. In one embodiment, the cDNA sequence encoding for the light chain variable region has at least 95% sequence homology to the nucleotide sequence of SEQ ID NO.: 4. In one embodiment, the cDNA sequence encoding for the light chain variable region has at least 96% sequence homology to the nucleotide sequence of SEQ ID NO.: 4. In one embodiment, the cDNA sequence encoding for the light chain variable region has at least 97% sequence homology to the nucleotide sequence of SEQ ID NO.: 4. In one embodiment, the cDNA sequence encoding for the light chain variable region has at least 98% sequence homology to the nucleotide sequence of SEQ ID NO.: 4. In one embodiment, the cDNA sequence encoding for the light chain variable region has at least 99% sequence homology to the nucleotide sequence of SEQ ID NO.: 4.

In one embodiment, the nucleotide sequence encodes for one or more CDRs. In one embodiment, the nucleotide sequence encoding for one or more CDRs comprises a nucleotide with at least 85% sequence homology to the nucleotide sequence of SEQ ID NO.: 5, SEQ ID NO.: 6, SEQ ID NO.: 7, SEQ ID NO.: 11, SEQ ID NO.: 12, and/or SEQ ID NO.: 13. In one embodiment, the nucleotide sequence encoding for one or more CDRs comprises a nucleotide with at least 90% sequence homology to the nucleotide sequence of SEQ ID NO.: 5, SEQ ID NO.: 6, SEQ ID NO.: 7, SEQ ID NO.: 11, SEQ ID NO.: 12, and/or SEQ ID NO.: 13. In one embodiment, the nucleotide sequence encoding for one or more CDRs comprises a nucleotide with at least 96%, 97%, 98%, or 99% sequence homology to the nucleotide sequence of SEQ ID NO.: 5, SEQ ID NO.: 6, SEQ ID NO.: 7, SEQ ID NO.: 11, SEQ ID NO.: 12, and/or SEQ ID NO.: 13. In a preferred embodiment, the nucleotide sequence encoding for one or more CDRs comprises the nucleotide sequence of SEQ ID NO.: 5, SEQ ID NO.: 6, SEQ ID NO.: 7, SEQ ID NO.: 11, SEQ ID NO.: 12, and/or SEQ ID NO.: 13. In an especially preferred embodiment, the nucleotide sequence comprising the nucleotide sequence of SEQ ID NO.: 5, SEQ ID NO.: 6, and/or SEQ ID NO.: 7 encodes for a CDR of the heavy chain variable region of the antibody construct or antibody fragment. In one embodiment, the nucleotide sequence comprising the nucleotide sequence of SEQ ID NO.: 5, SEQ ID NO.: 6, and/or SEQ ID NO.: 7 encodes for a CDR of the light chain variable region of the antibody construct or antibody fragment. In one embodiment, the nucleotide sequence comprising the nucleotide sequence of SEQ ID NO.: 11, SEQ ID NO.: 12, and/or SEQ ID NO.: 13 encodes for a CDR of the heavy chain variable region of the antibody construct or antibody fragment. In an especially preferred embodiment, the nucleotide sequence comprising the nucleotide sequence of SEQ ID NO.: 11, SEQ ID NO.: 12, and/or SEQ ID NO.: 13 encodes for a CDR of the light chain variable region of the antibody construct or antibody fragment.

In one embodiment, the nucleotide sequence is a cDNA sequence. In one embodiment, the nucleotide sequence is an RNA molecule encoded by a nucleotide comprising SEQ ID NO.: 5, SEQ ID NO.: 6, SEQ ID NO.: 7, SEQ ID NO.: 11, SEQ ID NO.: 12, and/or SEQ ID NO.: 13. In one embodiment, the nucleotide sequence is an RNA molecule encoded by a nucleotide comprising SEQ ID NO.: 2. In one embodiment, the nucleotide sequence is an RNA molecule encoded by a nucleotide comprising SEQ ID NO.: 4.

The present invention further provides vectors comprising at least one nucleic acid encoding the light chain of the antibody construct or antibody fragment of the present invention and/or at least one nucleic acid encoding the heavy chain of the antibody construct or antibody fragment of the present invention. The nucleic acids may be either present in the same vector or may be present in the form of binary vectors. The vector preferably comprises the promoter operatively linked to the nucleic acid in order to facilitate expression of the nucleic acid encoding the light and/or heavy chain. Preferably, the vector also includes an origin for replication and maintenance in a host cell. The vector may also comprise a nucleotide sequence encoding a signal sequence located 5' of the nucleic acid encoding the light chain and/or heavy chain. The signal sequence may facilitate secretion of the encoded chain into the medium. The vector may further comprise a His-tag coding nucleotide sequence resulting in the expression of a construct for producing a fusion product with a His-tag at the N-terminus of the light and/or heavy chain of the antibody construct or antibody fragment, which facilitates purification of the protein.

In one embodiment, the antibody construct or antibody fragment according to the present invention is modified. The modifications include the di-, oligo-, or polymerization of the monomeric form e. g. by cross-linking using dicyclohexylcarbodiimide. The di-, oligo-, or polymers can be separated from each other by gel filtration. Further modifications include side chain modifications, e. g. modifications of ε-amino-lysine residues, or amino and carboxy-terminal modifications, respectively. Further modifications include post-translational modifications, e.g. glycosylation and/or partial or complete deglycosylation of the protein, and disulfide bond formation. The antibody construct or fragment may also be conjugated to a label, such as an enzymatic, fluorescent or radioactive label.

In one embodiment, the antibody construct or antibody fragment is a chimeric antibody. In one embodiment, the antibody construct or antibody fragment is a humanized antibody. In a preferred embodiment, the antibody construct or antibody fragment is a human antibody. In an especially preferred embodiment, the antibody construct or antibody fragment is a fully human antibody.

In one embodiment, the antibody construct or antibody fragment is lyophilized.

In one aspect, this invention relates to a pharmaceutical composition comprising the antibody construct or antibody fragment as described herein. Such compositions include various excipients, diluents, carriers, and such other inactive agents well known to the skilled artisan. In one embodiment, the pharmaceutical composition comprises the antibody construct or antibody fragment and a pharmaceutically acceptable carrier, diluent, or excipient.

Methods of Making Antibody Constructs and Fragments Thereof

This invention further relates to methods and composition for making the antibody construct or antibody fragment as described herein.

In one embodiment, human B-cells are obtained from patients who have been exposed to RSV and/or RSV F protein (e.g., convalescing patients or patients immunized with F protein or a fragment thereof). Blood samples can be taken from the patients and human B-cells can be isolated in a known manner (e.g., Current Protocols in Immunology. Chapter 7.1. Isolation of whole mononuclear cells from peripheral blood and cord blood. Published by Wiley & Sons, Eds: J C Coligan et al.). In one embodiment, the human B-cell may be fused to a myeloma or heteromyeloma to produce a hybridoma in accordance with known techniques according to the classical Kohler and Milstein approach, as described by Lang et al. "Prophylaxis and therapy of *Pseudomonas aeruginosa* infection in cystic fibrosis and immunocompromised patients" Vaccine, 22: S44-S48 (2004), which is incorporated herein by reference in its entirety. In a preferred embodiment, the B cell is cultured and the cDNA sequence of a heavy chain variable region, light chain variable region, and/or one or more CDRs is isolated therefrom. The cDNA sequences can be used to generate one or more vectors. Methods of producing fully human antibodies are described, for example, in Beerli et al. "Isolation of Human Monoclonal Antibodies by Mammalian Cell Display," *PNAS* 105(38): 14336-14341 (2008), which is incorporated herein by reference in its entirety.

The vector(s) can be introduced into a cell such that the cell produces the antibody construct, antibody fragment, or portion thereof. The cell may be a prokaryotic cell or a eukaryotic cell. In a preferred embodiment, the cell is a plant cell or a mammalian cell. In one embodiment, the cell is a human cell. In one embodiment, the cell is a HEK293 cell. In one embodiment, the cell is a PerC6 cell, a CHO cell, a COS cell, or a HELA cell.

In one embodiment, the antibody construct or antibody fragment described herein is produced in a plant cell. Methods of producing antibodies in plant cells are described, for example, in U.S. Pat. Nos. 8,119,406 and 8,513,397, each of which is incorporated herein by reference in its entirety. In a preferred embodiment, the cell is from a tobacco plant (e.g., genus *Nicotiana*).

Preferably, the host cell comprises at least one nucleic acid encoding the light chain and at least one nucleic acid encoding the heavy chain and is capable of assembling the antibody construct such that a 3-dimensional structure is generated which is equivalent to the 3-dimensional structure of a human antibody produced by a human B-cell. If the light chain is produced separately from the heavy chain, then both chains may be purified and subsequently be assembled to produce an antibody having essentially the 3-dimensional structure of a human antibody as produced by a human B-cell. Alternatively, the host cell comprises at least one nucleic acid encoding at least the antigen-binding portion of the light chain and at least one nucleic acid encoding at least the antigen-binding portion of the heavy chain, and is capable of assembling the antibody construct or fragment such that the antibody construct or fragment is capable of binding the antigen.

The antibody construct or antibody fragment may also be obtained by recombinant expression of the encoded light and/or heavy chain (or portion thereof), wherein the nucleic acid is produced by isolating a nucleic acid encoding a human antibody and grafting of the nucleic acid sequence encoding the CDRs as defined in the figures onto the isolated nucleic acid.

Antibodies or antibody fragments can be purified, for example from cell culture supernatant, by any method. Exemplary methods of antibody purification are described in Liu et al., "Recovery and purification process development for monoclonal antibody production," *mAbs* 2(5): 480-499 (2010), which is incorporated herein by reference in its entirety.

In one aspect, this invention relates to a chromatography column or membrane comprising an antibody construct or antibody fragment as described herein, wherein the antibody construct or antibody fragment is bound to the chromatography column or membrane. In one embodiment, the chromatography column or membrane comprises Protein A, e.g. a Protein A resin. In one embodiment, the chromatography column or membrane comprises an ion exchange resin. In one embodiment, the chromatography column or membrane comprises a hydrophobic charge induction chromatography column.

Although the descriptions and examples herein are directed to production of the antibody construct or fragment within a single cell or cell line, it is contemplated that one or more portions of the antibody construct or fragment may be produced by separate cells or cell lines and then combined to form a functional antibody construct or fragment. For example, the heavy chain (or portion thereof) may be produced by one cell, and the light chain (or portion thereof) may be produced by a second cell. The components may be isolated or purified, e.g. from the cell culture supernatant, and covalently or non-covalently linked by routine methods.

In one embodiment, this invention relates to a method for determining the potency of a putative antibody to strains of RSV that are resistant to commercially available antibodies, e.g., palivizumab. The binding affinity, neutralizing capacity, antigenicity, or any other measure of the usefulness of the putative antibody against at least one RSV strain may be compared to the antibody construct of the current invention. In one embodiment, a putative antibody that is determined to bind with an affinity equal to or greater than, have a neutralization capacity equal to or greater than, and/or exhibit equal or less antigenicity than, an antibody construct as described herein is further tested for effectiveness against RSV.

Methods of Treatment

This invention further relates to methods of treatment using the antibody construct or antibody fragment as described herein.

In one aspect, this invention relates to methods of preventing RSV infection in a patient at risk of infection by RSV. In one embodiment, upper respiratory infection is prevented. In one aspect, lower respiratory infection is prevented. In one aspect, both upper and lower respiratory infection is prevented.

In one aspect, this invention relates to methods of treating RSV infection in a patient. In one embodiment, upper respiratory infection is treated. In one aspect, lower respiratory infection is treated. In one aspect, both upper and lower respiratory infection is treated.

In one embodiment, the patient is a human. In a preferred embodiment, the patient is an infant (e.g., under 12 months of age). In one embodiment, the patient is a human having a condition that increases the risk of RSV infection. Conditions that increase the risk of RSV infection include, but are not limited to, being under 6 months of age; being under 12 months of age and born prematurely (e.g., before 40 weeks gestational age); lung disease; chronic obstructive pulmonary disease; congenital heart disease; congestive heart failure; weakened immune system; asthma; immunodeficiency (e.g., transplanted organ, leukemia, HIV/AIDS).

In one embodiment, the antibody construct or antibody fragment is administered to a patient at risk of infection by RSV. In one embodiment, the antibody construct or antibody fragment is administered to a patient having or believed to have an infection by RSV. In one embodiment, a therapeutically effective amount of the antibody construct or antibody fragment is administered. In one embodiment, the therapeutically effective amount is between about 1 mg per kg body weight and about 1000 mg per kg body weight. In a preferred embodiment, the therapeutically effective amount is between about 1 mg per kg body weight and about 100 mg per kg body weight. In a more preferred embodiment, the therapeutically effective amount is between about 5 mg per kg body weight and about 50 mg per kg body weight. It is to be understood that the amount can be a range between any two of these values, or any value there between (including endpoints).

The antibody construct or antibody fragment may be administered by any appropriate route. The compositions, provided herein or known, suitable for administration in accordance with the methods provide herein, can be suitable for a variety of delivery modes including, without limitation, intramuscular and intravenous delivery. Compositions suitable for internal, pulmonary, rectal, nasal, vaginal, lingual, intraarterial, intraperitoneal, intracutaneous and subcutaneous routes may also be used. Sustained release dosage forms may also be used. All dosage forms may be prepared using methods that are standard in the art (see e.g., Remington's Pharmaceutical Sciences, 16th ed., A. Oslo editor, Easton Pa. 1980).

In one embodiment, the antibody construct or fragment is administered once. In a preferred embodiment, the antibody construct or fragment is administered multiple times. In a more preferred embodiment, the antibody construct or fragment is administered once a month during RSV season. RSV season is generally November through April (in the Northern Hemisphere), but can be longer depending on the area and other factors (e.g., the primary strains that are circulating in a given year).

In one embodiment, the invention relates to a bag for intravenous delivery, comprising an IV bag containing the antibody construct or antibody fragment and a pharmaceutically acceptable excipient.

EXAMPLES

Unless stated otherwise, the abbreviations used throughout the specification have the following meanings

| | |
|---|---|
| cDNA = | complimentary deoxyribonucleic acid |
| CDR = | complementarity determining region |
| ELISA = | enzyme-linked immunosorbent assay |
| FCS = | fetal calf serum |
| g = | gram |
| HC = | heavy chain |
| HRP = | horseradish peroxidase |
| Ig = | immunoglobulin |
| KD = | dissociation constant |
| kg = | kilogram |
| LC = | light chain |
| M = | molar |
| mAb = | monoclonal antibody |
| mg = | milligram |
| min = | minute |
| mL = | milliliter |
| mM = | millimolar |
| ng = | nanogram |
| nM = | nanomolar |
| PBS = | phosphate buffer saline |
| PCR = | polymerase chain reaction |
| pM = | picomolar |
| RNA = | ribonucleic acid |
| RSV = | respiratory syncytial virus |
| RT-PCR = | reverse transcription PCR |
| µg = | microgram |
| µL = | microliter |
| µM = | micromolar |
| ° C. = | degree Celsius |

These one-letter symbols have the following meaning when representing amino acids:

| | |
|---|---|
| A = | Alanine |
| R = | Arginine |
| N = | Asparagine |
| D = | Aspartic acid |
| C = | Cysteine |
| E = | Glutamic acid |
| Q = | Glutamine |
| G = | Glycine |
| H = | Histidine |
| I = | Isoleucine |
| L = | Leucine |
| K = | Lysine |
| M = | Methionine |
| F = | Phenylalanine |
| P = | Proline |
| S = | Serine |
| T = | Threonine |
| W = | Tryptophan |
| Y = | Tyrosine |
| V = | Valine |

When representing nucleic acids, A=Adenine; T=Thymine; C=Cytosine; G=Guanine; U=Uracil, N=any nucleic acid.

The following Examples are intended to further illustrate certain embodiments of the disclosure and are not intended to limit its scope.

Example 1

Selection of Human B-Cells Specific for RSV

For the generation of an antibody construct specific for the RSV F protein, human lymphocytes from recently resected tonsils of human infants were isolated by mechanical disruption and passaging through a cell strainer. Isolated lymphocytes were depleted in parallel from monocytes by plastic adhesion in cell culture flasks, and subsequently RSV specific B cells were enriched by incubation of lymphocytes with immobilized total RSV antigen. For this purpose, 6-well plates were coated with total RSV antigen (EIA-antigen) at 10 µg/mL in phosphate buffer saline (PBS) overnight. After coating, the wells were blocked by incubation with 10% fetal calf serum (FCS) in PBS. Between one and ten million monocyte-depleted cells were incubated per one well of the coated six-well plate. Following incubation for one hour, the wells were washed and bound cells were harvested by trypsinization. The cells were added to plates containing cell culture medium containing 10% FCS and 10% conditioned supernatant with 20,000 EL-4B5 feeder cells (kind gift from the Geneva University Hospital, Geneva, Switzerland) that had been irradiated at 5000 cGy by a Gammacell 40 Research Irradiator. Conditioned supernatant was generated by stimulating isolated peripheral blood lymphocytes with phytohaemagglutinin (PHA, 5 µg/mL) and phorbol myristate acetate (PMA, 10 ng/mL) for 36 hours, followed by removal of cells and debris prior to cryopreservation. The conditioned supernatant was thawed prior to addition to the RSV-EIA selected lymphocytes. After up to ten days, small aliquots of the cell culture supernatants were analyzed for specific antibodies by RSV EIA ELISA.

ELISA plates were coated with RSV-EIA antigen or purified RSV F protein (Human RSV (A2) Fusion glycoprotein RSV F protein, Sino Biological Inc., Beijing, China) at 0.5 pg/mL overnight at 4° C., then blocked with 0.5% BSA in PBS. Cell culture supernatants were diluted with PBS containing 0.05% Tween (PBS-Tween) and aliquoted into wells. After incubation and subsequent washing with PBS-Tween, horseradish peroxidase-(HRP) labeled goat anti-human IgG was used to detect human IgG bound to the antigen. Positive wells were identified by colorimetric measurement, and cells from positive wells were expanded at low density in the presence of irradiated feeder cells and cell culture medium containing 10% FCS and 10% conditioned supernatant (as described above) over a period of several days. After retesting supernatants for specificity to RSV F protein, cells from positive wells were collected and processed for RNA isolation.

Example 2

Generation of Human Monoclonal Antibody to RSV

The method for isolating the specific antibody is summarized in FIG. 1. Specifically, RNA from selected B-cells was used to generate 5'RACE cDNA, followed by isotype specific RT-PCR to identify the variable region of the heavy chain (HC) and light chain (LC) as described by Welschof et al. "Amino acid sequence based PCR primers for amplification of rearranged human heavy and light chain immunoglobulin" Journal of immunological methods 179(2): 203-214 (1995). The variable region of the HC was combined by PCR with the constant region of an IgG1 which is essentially in accordance with the IMGT reference sequence Y14737 (Lefranc, M.-P. et al., 2001 The Immunoglobulin Facts Book Academic Press, London, UK) and cloned into the eukaryotic expression vector pcDNA3.3-Topo (Invitrogen, USA). The whole coding region of the LC was amplified by RT-PCR and cloned into the expression vector. Subsequently, the vectors were transiently transfected into HEK293T cells [ATCC #CRL-11268 (American Type Culture Collection (ATCC), Manassas, Va. 20110 USA)]. Four to five days after transfection, supernatants were tested by ELISA for presence of antigen-binding antibodies as described above. The most promising candidate, AR201 (also called KBRV201), was selected for sequencing of the variable regions of the heavy and light chains. The final vectors were amplified and analyzed by Sanger sequencing.

The nucleotide and corresponding amino acid sequences are provided in FIGS. 2 (heavy chain, SEQ ID NO.: 1 and 2) and 3 (light chain, SEQ ID NO.: 3 and 4). The nucleotide and corresponding amino acid sequences of individual CDR regions are provided in FIGS. 4 (heavy chain: CDR1, SEQ ID NO.: 5 and 8; CDR2, SEQ ID NO.: 6 and 9; CDR3, SEQ ID NO.: 7 and 10) and 5 (light chain: CDR1, SEQ ID NO.: 11 and 14; CDR2, SEQ ID NO.: 12 and 15; CDR3, SEQ ID NO.: 13 and 16).

Example 3

Binding of Human Monoclonal Antibody to RSV F Protein Antigen

The isolated and sequenced human antibody AR201 was tested for binding characteristics to RSV F protein, as shown in FIG. 6. Hek293T cells were seeded at 300,000 cells per well of a six-well plate and cultivated overnight. After one day, medium was exchanged, and a freshly prepared solution of expression plasmids was added carefully to the cells. Cells were incubated for another 24 hours and medium was exchanged again for Pro293a-CDM medium. After three to five days, the resulting supernatant containing recombinant antibody was collected and antibody was purified by affinity chromatography with a HiTrap Protein A sepharose affinity column (GE Healthcare Life Sciences, Pittsburgh, Pa., USA). Resulting antibody was stored at −20° C. until use. For binding experiments, ELISA plates were coated as described above, and serial dilutions of purified AR201 or an unrelated fully human monoclonal IgG1 antibody (control) were added. After careful washing, bound antibodies were detected with anti-human IgG-HRP labeled secondary antibody. EC50 values were calculated based on colorimetric measurement of the bound antibody applying a variable slope-four parameter equation (GraphPad Prism Software V5.02, GraphPad Software Inc. San Diego, Calif., US). The EC50 value of AR201 was calculated as 0.1031 nM. No EC50 value could be calculated for the control monoclonal human IgG1 antibody.

Example 4

Affinity Measurement of AR201

Kinetic characterization of the interaction of AR201 versus a commercially available antibody specific for RSV F protein (palivizumab) was conducted by surface plasmon resonance (Biaffin GmbH, Kassel, Germany). AR201 was produced and purified as described above. Recombinant human RSV F protein was covalently immobilized via amine coupling to a CM5 sensor chip for kinetic characterization of the interaction with the antibodies using surface plasmon resonance on a Biacore 2000 instrument (GE Healthcare, Biacore AB, Uppsala, Sweden). For the kinetic analysis of the antibody AR201, dilutions of AR201 antibody were prepared starting at 100 nM and ending at 49 pM after twelve 1:1 dilutions in running buffer. Samples were injected for an association time of two min, and dissociation was monitored upon switching to running buffer for 30 min at a flow rate of 30 pL/min. Bound antibody was removed after each injection by surface regeneration using 100 mM HCl (3×10 sec). Data evaluation was performed by global fitting of the binding curves assuming a Langmuir 1:1 binding model using the Biacore Evaluation software version 4.1. The determined dissociation constant (KD) for AR201 is 58±6 pM. In comparison, palivizumab has a significantly lower KD value of 960 pM (www.ema.europa.eu/docs/en_GB/document_library/EPAR_-_Scientific_Discussion/human/000257/WC500056731.pdf). Results are provided in Table 1.

TABLE 1

Association and dissociation constants for AR201.

| Analyte | $k_{diss}$ in s$^{-1}$ | $k_{ass}$ in M$^{-1}$ s$^{-1}$ | $K_D$ in M |
|---|---|---|---|
| AR201 | $(2.7 \pm 0.1) \times 10^{-5}$ | $(4.7 \pm 0.5) \times 10^{5}$ | $(5.8 \pm 0.6) \times 10^{-11}$ |

Example 5

Binding of AR201 to RSV Reference Strains

Figure 7:
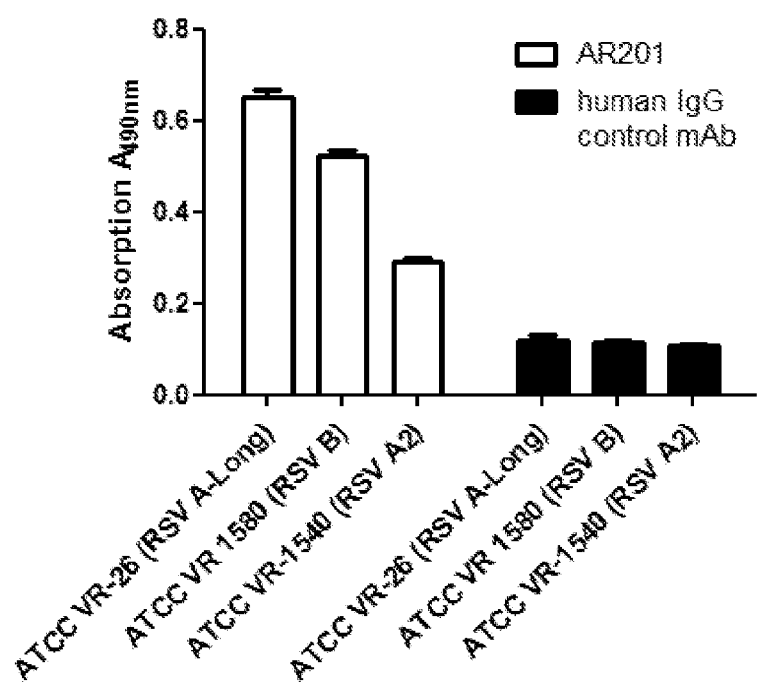
FIG. 7 describes the recognition and binding of reference strains of RSV-A and RSV-B by AR201.

The binding of AR201 to RSV reference strains was tested by ELISA assay. The RSV reference strains RSV-A Long (ATCC VR-26), RSV-B (ATCC VR 1580) and RSV-A2 (ATCC VR-1540) were all purchased from LCG (LGC Standards S.a.r.l., Molsheim, France) and amplified in Vero cells. Subsequently, the supernatant of positive wells was cryopreserved at −80° C. until further use. For the ELISA, assay plates were coated with a polyclonal anti-RSV antibody at 500 ng/ml. Meanwhile, 10 µg/ml AR201 or human monoclonal IgG1 isotype control antibody were incubated with RSV at a 1:10 dilution of the frozen amplified RSV strains. After 1 hour, the immune complexes were transferred to the coated ELISA plates and a secondary anti-human IgG-HRP labeled antibody was added. Bound human IgG was detected by colorimetric measurement. As shown in FIG. 7, all three reference strains are recognized by AR201.

Example 6

Neutralization of Reference Strains by AR201

The neutralization of RSV reference strains by AR201 and palivizumab was tested in an infectivity assay. Virus stock (25-250 pfu/well) of the reference strains RSV-A Long (ATCC VR-26) and RSV-B (ATCC VR 1580) was incubated with a two-fold dilution series of antibody solution, and then added to Vero cells that had been seeded in 24-well plates the day before. After four hours, the inoculum was replaced by a semi-solid agarose overlay and incubated for another three days. Subsequently, cells were fixed and stained by immunohistochemistry for the presence of RSV-specific plaques. The percentage of neutralization for each concentration of the RSV-specific antibodies was calculated based on the number of plaques per well. Based on the concentration of the antibody stock, the minimal neutralizing antibody concentration achieving >50% virus neutralization was calculated. As shown in Table 2, AR201 was at least twice as efficient in neutralizing viral particles of either strain and preventing the formation of syncytia indicative of an active, reproductive infection, as compared to palivizumab. An IgG isotype human monoclonal control antibody had no effect on the prevention of infections of Vero cells with either of the RSV reference strains.

TABLE 2

Estimated half-maximal effective antibody concentration (ng/mL).

| | Palivizumab | AR201 | Isotype control | Ratio Palivizumab/AR201 |
|---|---|---|---|---|
| RSV-A/Long | 100 ng/ml | 40 ng/ml | >1000 | 2.5 |
| RSV-B | 200 ng/ml | 100 ng/ml | >1000 | 2 |

Example 7

Binding of AR201 to Clinical Isolates of RSV

Figure 8A:
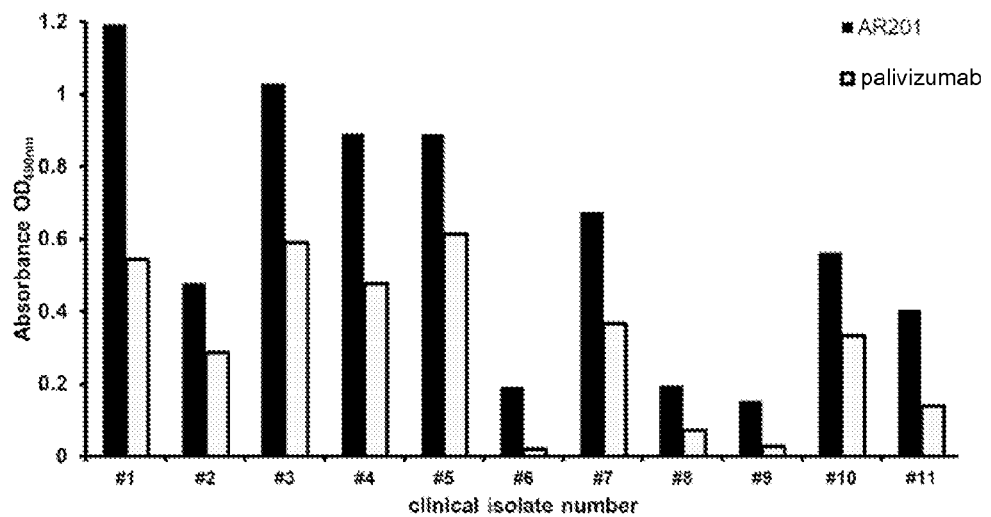
FIGS. 8A and 8B compares the recognition of clinical isolates of RSV by AR201 (black bars) and palivizumab (white bars).
Figure 8B:
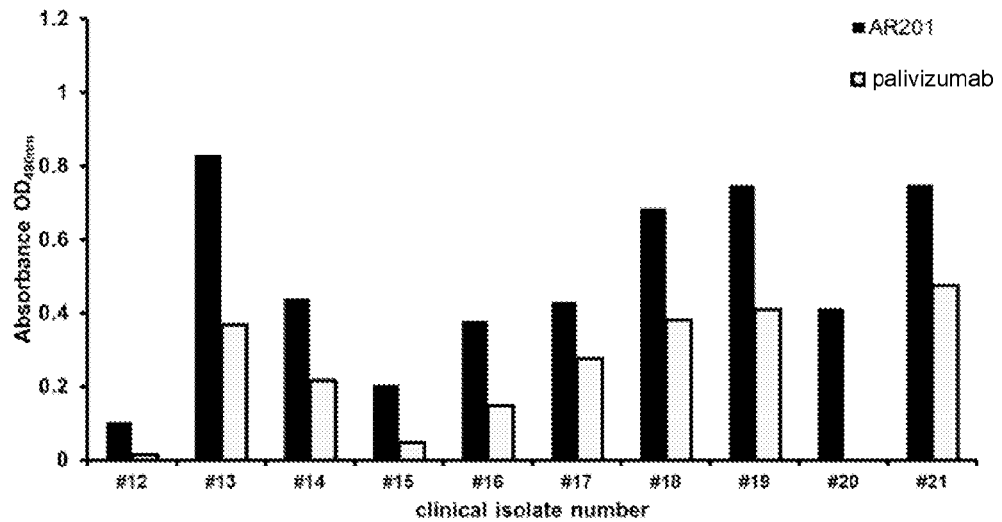

The recognition of fresh isolated clinical RSV isolates by AR201 was tested by ELISA assay. Clinical RSV isolates (21 separate isolates) were collected from nasopharyngeal mucus from patients testing positive for RSV. The collected mucus was cultured by incubation on Vero cells, and supernatant of positive wells (as identified by formation of syncytia) were serially passaged twice onto fresh Vero cells. Supernatant of positive wells was cryopreserved at −80° C. until further use. For binding analysis, ELISA plates were coated with individual RSV isolates (diluted 1:10), and subsequently incubated with AR201, palivizumab, or a human monoclonal IgG isotype control antibody, at 1 µg/mL. A secondary anti-human IgG-HRP labeled antibody was added to each well. Bound human IgG was detected by colorimetric measurement. The background absorbance, as determined by the signal of the control IgG monoclonal antibody, was deducted twice from the signal detected with AR201 or palivizumab and any absorbance value greater than 0.1 was considered a positive signal. The experiment was repeated three times; a representative experiment is shown in FIGS. 8A and 8B. AR201 recognized all 21 clinical isolates to varying extent, whereas palivizumab always showed a lesser signal intensity. In order to identify palivizumab-resistant strains, the ratio of the binding signal of AR201 over palivizumab was analyzed. Any clinical isolate with a binding signal ratio of 5 or greater of AR201 over palivizumab was considered a palivizumab-resistant isolate.

Figure 8C:
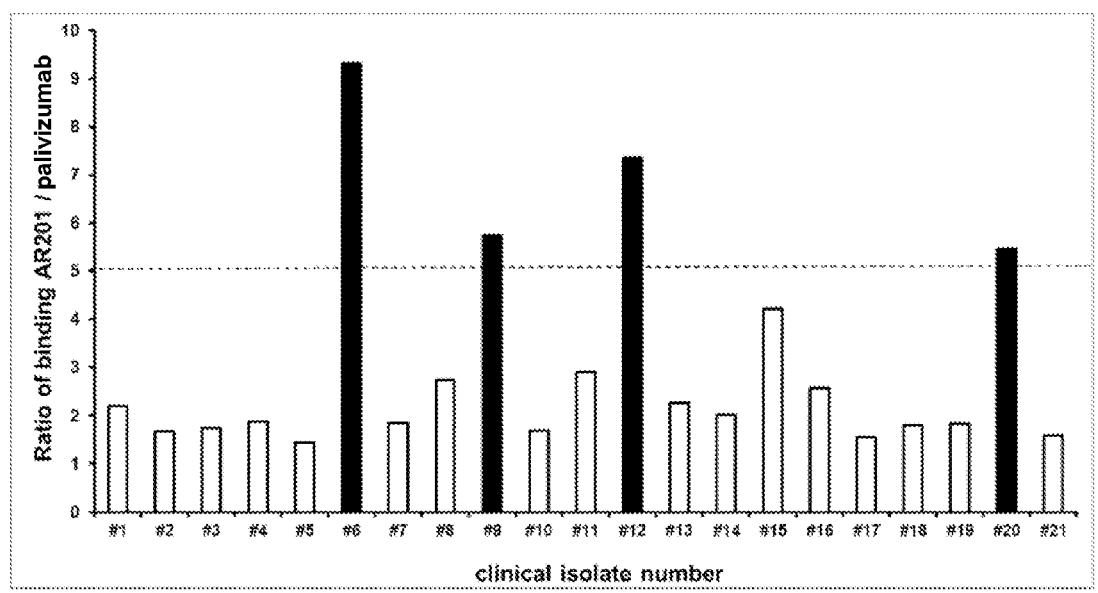
FIG. 8C indicates the ratio of binding of AR201 and palivizumab to clinical isolates of RSV. Black bars indicate a binding ratio of greater than 5 for the binding of AR201 over palivizumab to the respective clinical RSV isolate, indicative of resistance of the clinical isolate towards palivizumab.

The results of the analysis are shown in FIG. 8C and Table 3. Palivizumab failed to recognize 4 of the 21 isolates, notably the clinical isolates #6, #9, #12 and #20. Clinical isolate #20 had a ratio just above 5.

TABLE 3

Recognition of clinical RSV isolates.

| Monoclonal Antibody | Recognition of clinical isolate |
|---|---|
| AR201 | 21/21 |
| Palivizumab | 17/21 |
| Human IgG control mAb | 0/21 |

Example 8

Neutralization of Clinical Isolates by AR201

The neutralization of two clinical RSV isolates (isolate #1 and #20) by AR201 and palivizumab was tested in an infectivity assay. The two RSV isolates were amplified on Vero cells and supernatant cryopreserved until further use. The dilution of the stock solution achieving a 50% infectivity rate in a tissue culture (TCID) was calculated based on the Spearman and Kärber algorithm (Hierholzer J C et al., 1996, in *Virology Methods Manual*, edited by B M J Mahy and H O Kangro, London: Academic Press, p. 47). Virus stock were thawed and diluted to 10×TCID50, and incubated with serial dilutions of antibodies AR201, palivizumab, or IgG1 isotype human control monoclonal antibody. The mixture was added to confluent Hep2 cells (ATCC CCL-23) in 96-well plates and incubated for four days. Cells were fixed and infected cells were detected with an anti-RSV mouse monoclonal antibody clone 631 (Milan Analytica AG, Switzerland). The rate of infection and IC50 values were calculated based on colorimetric measurement of the bound antibody by applying a variable slope-four parameter equation (GraphPad Prism Software V5.02, GraphPad Software Inc. San Diego, Calif., US). The IC50 served as measure of the neutralization activity. IC50 is the antibody concentration (g/mL) that neutralizes the infectivity capacity of an RSV infective dose by 50%.

Results are shown in Table 4. AR201 had an IC50 that was 18 times lower than palivizumab for isolate #1. For isolate #20, no neutralization capacity was observed for palivizumab, confirming that palivizumab does not bind to clinical isolate #20, whereas AR201 showed a similar IC50 on isolate #20 as seen with isolate #1.

TABLE 4

IC50 of AR201 and palivizumab for clinical isolates #1 and #20.

| IC50 microM | RSV-Isolate 1 | RSV-Isolate 20 |
|---|---|---|
| AR201 | 1.702 | 1.706 |
| Palivizumab | 30.601 | >1000 |
| IgG1 Isotype control | >1000 | >1000 |
| Ratio palivizumab/AR201 | 18.0 | n/a |

Example 9

Sequencing of F Protein Sequence of the Palivizumab-Resistant Clinical Isolate #20

The nucleotide and amino acid sequences of the F protein of clinical isolate #20 were determined. RNA was isolated from amplified clinical isolate #20 and cDNA was generated with F protein specific primers (Primer RSV-A F protein: GAAATTAAACCTGGGGCAAATAACC [SEQ ID NO.: 19]; Primer RSV-B F protein: ACAAAAT-MAACTCTGGGGCAAATAAC [SEQ ID NO.: 20]). The resulting fragment (expected size: 1935 bp) was amplified using specific primers (RSV-7607: CTTCGYGA-CATATTTGCCCCAG [SEQ ID NO.: 21]; ZhaoF: GGGGCAMTMCMTGGAGTTGC [SEQ ID NO.: 22]). Amplified DNA was sequenced by Sanger sequencing at Microsynth (Balgach, Switzerland).

The nucleotide sequence of the coding region for the F protein of clinical isolate #20 (SEQ ID NO.: 17) is provided in FIG. 9A. The corresponding amino acid sequence (SEQ ID NO.: 18) is provided in FIG. 9B.

Comparison to the published sequence of the postulated epitope of palivizumab (McLellan J S. et al., 2010), identified as the sequence of amino acids 254 to 277 of the RSV F protein A2 strain, revealed a mutation of lysine at the position 272 to asparagine (K272N) for the clinical isolate #20, as shown in FIG. 10. A mutation at position 272 from lysine to another amino acid was described earlier as critical for loss of binding of palivizumab to the F protein (Zhu, et al., 2011; Adams et al., 2010), confirming the inability of palivizumab to bind to clinical isolate #20.

Example 10

Cross Inhibition on RSV Clinical Isolates with AR201 and Palivizumab

Palivizumab is the only anti-RSV monoclonal antibody that has been approved by the FDA to date for the prevention of RSV infection in infants and neonates. Palivizumab binds to antigenic region A on the F protein of RSV and inhibits fusion events of RSV with human lung epithelial cells.

Efficient cross-inhibition of binding of two independent monoclonal antibodies can only occur if both antibodies recognize the same epitope, or epitopes in close proximity, such that one antibody when bound to its epitope exerts steric hindrance for binding of the other antibody.

Intact RSV particles were pre-incubated with competitor antibody (palivizumab, AR201, or control at 20 μg/mL) for one hour and subsequently added to polystyrene ELISA plates that had been coated with either palivizumab or AR201. After incubation for one hour at 4° C., plates were washed and polyclonal rabbit-anti-RSV-HRP labeled antisera was added to each well. Bound viral particles were detected by colorimetric measurement. Maximum binding of RSV to the immobilized antibody in the presence of the competitor antibody was determined relative to binding in the presence of the monoclonal human IgG control antibody.

Results are provided in Table 5. Pre-incubation of RSV viral particles with AR201 reduced binding to AR201 coated plates to 22.5%, whereas pre-incubation with palivizumab affected binding to AR201 coated plates less and reduced the signal to only 29.2% of the control value. Vice versa, pre-incubation of RSV viral particles with AR201 reduced binding of RSV to palivizumab-coated plates to 40.8%, whereas pre-incubation with palivizumab reduced binding to palivizumab-coated plates at a slightly lower level, 35.3%.

These results indicate that AR201 targets the identical antigenic region on RSV F protein as palivizumab. Nevertheless, the difference in cross-inhibition indicates that AR201 recognizes an epitope very similar to or close to the epitope of palivizumab, but not the identical epitope.

TABLE 5

Cross-inhibition of AR201 or palivizumab for binding of RSV to antibody-coated plates

| | Coating mAb | |
|---|---|---|
| Inhibiting mAb | palivizumab | AR201 |
| AR201 | 40.8% | 22.5% |
| palivizumab | 35.3% | 29.2% |
| control IgG mAb | 100.0% | 100.0% |

Example 11

Protease Digestion of F Protein

Asp-N is an endoprotease which selectively cleaves peptide bonds N-terminal to aspartic acid residues. Asp-N digestion of the RSV F protein will cut the postulated palivizumab epitope N-terminal of amino acid positions 263 and 269, generating two protein fragments of 62 amino acids and 40 amino acids in length. Each peptide contains only a portion of the intact epitope for palivizumab, as shown in FIG. 11.

Purified recombinant F protein was incubated for 5 hours with Asp-N (Promega, Madison, Wis., US) at 37° C., according to manufacturer's instructions, in the presence of dithiothreitol (DTT) and iodacetamide, and subsequently coated onto ELISA plates. Antibody (AR201 or palivizumab) was added to the plate at two different concentrations, followed by addition of a polyclonal anti-human IgG-HRP labeled antibody. Bound antibody was detected based on colorimetric measurement.

Figure 12:
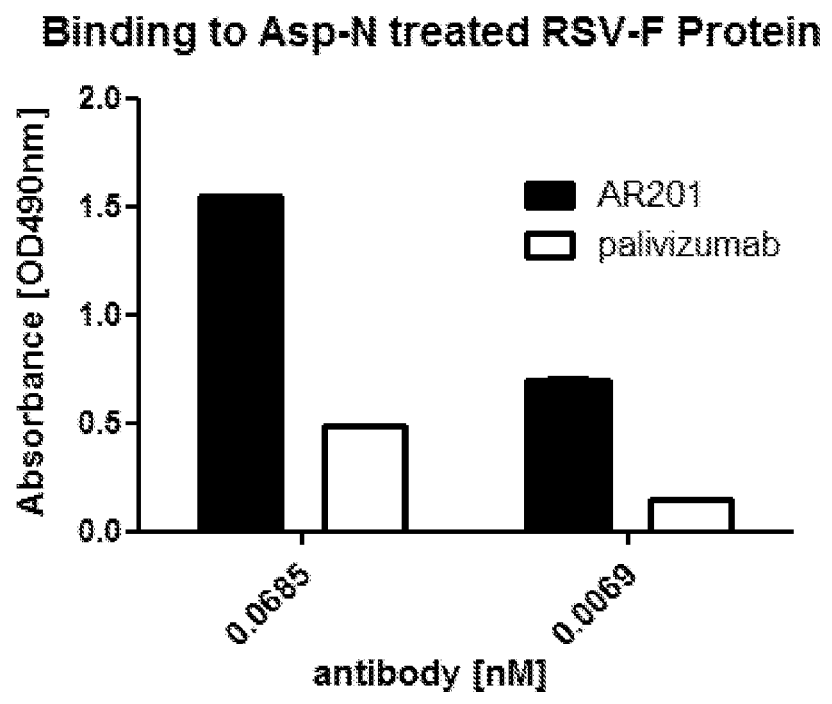

Palivizumab did not recognize any of the fragments of the complete digest of the RSV F protein, whereas AR201 still bound to as shown in FIG. 12. This demonstrates that the two antibodies do not share the same epitope, and AR201 recognizes an epitope distinct from amino acid sequence 254-277 of the RSV F protein.

All of the references described herein are incorporated by reference in their entireties.

What is claimed is:

1. A method of producing an antibody construct or antibody fragment, the method comprising culturing a cell under conditions in which cDNA sequences are expressed;
   wherein the cell comprises a first cDNA sequence which encodes a heavy chain variable region and a second cDNA sequence which encodes a light chain variable region, wherein the cell produces a human antibody construct or antibody fragment comprising the heavy chain variable region and the light chain variable region,
   wherein the heavy chain variable region encoded by the first cDNA sequence comprises (a) a heavy chain complementarity determining region (CDR)1 comprising the amino acid sequence GASINLYD (SEQ ID NO.: 8), (b) a heavy chain CDR2 comprising the amino acid sequence GYISGST (SEQ ID NO.: 9), and (c) a heavy chain CDR3 comprising the amino acid sequence ARDVGWGPQYYYGLDV (SEQ ID NO.: 10);
   wherein the light chain variable region encoded by the second cDNA sequence comprises (a) a light chain CDR1 comprising the amino acid sequence HSVQSTS (SEQ ID NO.: 14), (b) a light chain CDR2 comprising the amino acid sequence GGS (SEQ ID NO.: 15), and (c) a light chain CDR3 comprising the amino acid sequence QQSDRSPPIT (SEQ ID NO.: 16),
   and wherein the antibody construct or antibody fragment binds with specificity to RSV F protein antigenic region II/A with an affinity of greater than $1 \times 10^{-9}$ M.

2. The method of claim 1, wherein the neutralization capacity of the antibody construct or antibody fragment against at least one RSV strain is at least two times greater than the neutralization capacity of palivizumab.

3. The method of claim 1, wherein the cell is a plant cell or a mammalian cell.

4. The method of claim 1, wherein said heavy chain variable region cDNA sequence is coupled to a third cDNA sequence which encodes a constant region of human immunoglobulin.

5. The method of claim 4, wherein the third cDNA sequence is from a different patient than the first cDNA sequence and the second cDNA sequence.

6. The method of claim 4, wherein the human immunoglobulin is an IgG1.

7. The method of claim 1, wherein at least one expression vector is stably transfected into the cell and adapted to provide expression of the first cDNA sequence or the second cDNA sequence.

8. The method of claim 1, wherein at least one expression vector is transiently transfected into the cell and adapted to provide expression of the first cDNA sequence or the second cDNA sequence.

9. The method of claim 1, wherein the heavy chain variable region cDNA sequence comprises the nucleotide sequence of SEQ ID NO.: 2.

10. The method claim 1, wherein the light chain variable region cDNA sequence comprises the nucleotide sequence of SEQ ID NO.: 4.

11. The method of claim 1, wherein the first cDNA sequence comprises the nucleotide sequence of SEQ ID NO.: 5, SEQ ID NO.: 6, and/or SEQ ID NO.: 7, and further wherein the second cDNA sequence comprises the nucleotide sequence of SEQ ID NO.: 11, SEQ ID NO.: 12, and/or SEQ ID NO.: 13.

12. The method of claim 1, wherein the antibody comprises a heavy chain variable region comprising the amino acid sequence of SEQ ID NO.: 1.

13. The method of claim 1, wherein the antibody construct or antibody fragment comprises a light chain variable region comprising the amino acid sequence of SEQ ID NO.: 3.

14. The method of claim 1, wherein the antibody construct or antibody fragment recognizes the epitope of SEQ ID NO.: 23 and/or SEQ ID NO.: 24.

15. A method for treating an RSV infected patient, the method comprising administering a human antibody construct or antibody fragment to the patient, thereby treating the patient;
   wherein the antibody construct or antibody fragment comprises at least a heavy chain variable region and a light chain variable region,
   wherein the heavy chain variable region is encoded by a first cDNA sequence comprising (a) a heavy chain complementarity determining region (CDR)1 comprising the amino acid sequence GASINLYD (SEQ ID NO.:

8), (b) a heavy chain CDR2 comprising the amino acid sequence GYISGST (SEQ ID NO.: 9), and (c) a heavy chain CDR3 comprising the amino acid sequence ARD-VGWGPQYYYGLDV (SEQ ID NO.: 10), wherein the light chain variable region is encoded by a second cDNA sequence comprises (a) a light chain CDR1 comprising the amino acid sequence HSVQSTS (SEQ ID NO.: 14), (b) a light chain CDR2 comprising the amino acid sequence GGS (SEQ ID NO.: 15), and (c) a light chain CDR3 comprising the amino acid sequence QQSDRSPPIT (SEQ ID NO.: 16), and wherein the antibody construct or antibody fragment binds with specificity to RSV F protein antigenic region II/A with an affinity of greater than $1 \times 10^{-9}$ M.

16. The method of claim 15, wherein the human antibody construct or antibody fragment has a neutralization capacity against at least one RSV strain that is at least two times greater than the neutralization capacity of palivizumab.

17. The method of claim 15, wherein the human antibody construct or antibody fragment heavy chain variable region is coupled with a constant region of human immunoglobulin, provided that said constant region is not obtained from the same human from which the heavy chain CDR region was obtained.

18. The method of claim 15, wherein the human antibody construct or antibody fragment heavy chain variable region comprises the amino acid sequence of SEQ ID NO.: 1, and further wherein the light chain variable region comprising the amino acid sequence of SEQ ID NO.: 3.

19. The method of claim 15, wherein the human antibody construct or antibody fragment is administered with a pharmaceutically acceptable carrier, diluent, or excipient.

20. A method for preventing RSV infection in a patient at risk of infection with RSV, the method comprising administering an antibody construct or antibody fragment to the patient, thereby preventing the infection;

wherein the antibody construct or antibody fragment comprises at least a heavy chain variable region and a light chain variable region, wherein the heavy chain variable region is encoded by a first cDNA sequence comprising (a) a heavy chain complementarity determining region (CDR)1 comprising the amino acid sequence GASINLYD (SEQ ID NO.: 8), (b) a heavy chain CDR2 comprising the amino acid sequence GYISGST (SEQ ID NO.: 9), and (c) a heavy chain CDR3 comprising the amino acid sequence ARD-VGWGPQYYYGLDV (SEQ ID NO.: 10), wherein the light chain variable region is encoded by a second cDNA sequence comprises (a) a light chain CDR1 comprising the amino acid sequence HSVQSTS (SEQ ID NO.: 14), (b) a light chain CDR2 comprising the amino acid sequence GGS (SEQ ID NO.: 15), and (c) a light chain CDR3 comprising the amino acid sequence QQSDRSPPIT (SEQ ID NO.: 16), and wherein the antibody construct or antibody fragment binds with specificity to RSV F protein antigenic region II/A with an affinity of greater than $1 \times 10^{-9}$ M.

21. The method of claim 1, wherein the light chain and heavy chain are from different antibodies produced by the patient.

22. The method of claim 4, wherein the constant region is from other than the human producing the antibodies to RSV.

23. The method of claim 1, wherein the cell comprises one or more expression vectors, wherein the one or more expression vectors comprise the first cDNA sequence or comprise the second cDNA sequence.

24. The method of claim 1, wherein the cell produces an antibody fragment.

25. The method of claim 1, wherein the antibody construct or antibody fragment neutralizes at least one RSV strain that is resistant to palivizumab.

26. The method of claim 15, wherein the antibody construct or antibody fragment neutralizes at least one RSV strain that is resistant to palivizumab.

* * * * *